United States Patent
Deng et al.

(10) Patent No.: US 9,249,120 B2
(45) Date of Patent: Feb. 2, 2016

(54) CONJUGATED MICROPOROUS MACROMOLECULE CATALYST COMPLEXED WITH COBALT, PREPARATION AND USE THEREOF

(71) Applicant: DALIAN INSTITUTE OF CHEMICAL PHYSICS, CHINESE ACADEMY OF SCIENCE, Dalian (CN)

(72) Inventors: Weiqiao Deng, Dalian (CN); Yong Xie, Dalian (CN); Xiaohuan Liu, Dalian (CN)

(73) Assignee: DALIAN INSTITUTE OF CHEMICAL PHYSICS, CHINESE ACADEMY OF SCIENCES, Dalian (CN)

( * ) Notice: Subject to any disclaimer, the term of this patent is extended or adjusted under 35 U.S.C. 154(b) by 227 days.

(21) Appl. No.: 14/114,663

(22) PCT Filed: Oct. 15, 2012

(86) PCT No.: PCT/CN2012/082948
§ 371 (c)(1),
(2) Date: Oct. 29, 2013

(87) PCT Pub. No.: WO2013/091432
PCT Pub. Date: Jun. 27, 2013

(65) Prior Publication Data
US 2014/0066533 A1    Mar. 6, 2014

(30) Foreign Application Priority Data

Dec. 19, 2011  (CN) .......................... 2011 1 0427079
May 3, 2012  (CN) .......................... 2012 1 0135309
Aug. 1, 2012  (CN) .......................... 2012 1 0272056

(51) Int. Cl.
C07D 317/36     (2006.01)
B01J 31/22      (2006.01)
B01J 31/16      (2006.01)

(52) U.S. Cl.
CPC .......... *C07D 317/36* (2013.01); *B01J 31/1691* (2013.01); *B01J 31/2243* (2013.01); *B01J 31/2295* (2013.01); *B01J 2231/341* (2013.01); *B01J 2531/0252* (2013.01); *B01J 2531/16* (2013.01); *B01J 2531/26* (2013.01); *B01J 2531/31* (2013.01); *B01J 2531/62* (2013.01); *B01J 2531/845* (2013.01)

(58) Field of Classification Search
None
See application file for complete search history.

(56) References Cited

PUBLICATIONS

Xu et al. Chem. Eur. J. 2010, 16, 12898-12903.*

* cited by examiner

*Primary Examiner* — Yun Qian
(74) *Attorney, Agent, or Firm* — Enshan Hong; VLP Law Group LLP

(57) ABSTRACT

Disclosed are a type of catalyst which can catalyze the ring-addition reaction of $CO_2$ and an alkylene oxide at 0~180° C. under 0.1~8.0 MPa to produce a corresponding cyclic carbonate, and the preparation thereof. The catalyst is a conjugated microporous macromolecule polymer complexed with cobalt, chromium, zinc, copper or aluminum, and by using the macromolecule catalysts complexed with different metals to catalyze the reaction of $CO_2$ and alkylene oxide at normal temperature and normal pressure, a yield of the corresponding cyclic carbonate of 35%~90% can be obtained. The catalyst is easy to recover and the re-use of the catalyst has no influence on the yield; additionally, the yield can reach over 90% by controlling the reaction conditions.

8 Claims, 10 Drawing Sheets

US 9,249,120 B2

CONJUGATED MICROPOROUS MACROMOLECULE CATALYST COMPLEXED WITH COBALT, PREPARATION AND USE THEREOF

PRIORITY CLAIM

This is a U.S. national stage of application No. PCT/CN2012/082948, filed on Oct. 15, 2012. Priority is claimed on the following applications: Country: China, Application No.: 20110427079.2, Filed: Dec. 19, 2011; Country: China, Application No.: 201210135309.2, Filed: May 3, 2012; and Country: China, Application No.: 20120272056.3, Filed: Aug. 1, 2012, the content of which are incorporated here by reference.

FIELD OF THE INVENTION

In this invention, a series of new metals including Co, Cr, Zn, Cu, and Al coordinated conjugated microporous polymer catalysts were designed, synthesized, and used to catalyze the reaction of the epoxides and $CO_2$ to produce corresponding cyclic carbonates at mild conditions. Meanwhile, the catalysts can be recycled easily and reused for several times without reducing the yields, which obviously increases the utilization of catalysts.

BACKGROUND OF THE INVENTION

Carbon dioxide is one of the main greenhouse gases, but it is safe, nontoxic, inexpensive, and abundant. Since the industrial revolution, the carbon dioxide level in the atmospheric layer was rising year by year, enhancing the greenhouse effect, which leads to the globe warming and the frequent occurrence of the disastrous weather. Therefore, how to dispose and use CO2 has attracted the attention of the whole world. Recently, through the efforts of scientists around the world, it is the main strategy to conceive efficient carbon capture or conversion via chemical technologies. One of the most promising reactions in this area is the cycloaddition reaction of CO2 and epoxides to cyclic carbonates (CCs). However, numerous reported catalyst systems suffered from the harsh operation conditions and their catalytic activities were limited by the requirement of high pressure and temperature, together with the separation difficulties, which lead to the low efficiency to utilize them. Thus, the development of new effective catalytic systems for catalytic conversion with CO2 under mild conditions is desired, especially in real world applications.

SUMMARY OF THE INVENTION

In order to achieve the desire of the catalytic conversion of carbon dioxide under mild conditions, we designed and synthesized the cobalt, chromium, zinc, copper or aluminum-conjugated microporous polymer catalysts (CMP-1, CMP-2, CMP-3, CMP-4 and CMP-5, respectively) based on the previous research. The chemical conversion of $CO_2$ with epoxides to form corresponding cyclic carbonates using the CMP-1~5 catalyst system not only can obtain ideal effect at mild condition, but also can speed the production of cyclic carbonate at high temperature and pressure.

Synthesis methods for the cobalt, chromium, zinc, copper or aluminum-conjugated microporous polymer catalysts:

1. Synthesis of Salen:

With Monohydric alcohol (methanol or ethanol) as a solvent, a mixture solution of $R_1$-substituted salicylaldehyde and 1,2-diaminocyclohexane (mole ratio=1:1~30) was stirred for 3~15 hours at 0~150° C. to afford the Salen compounds.

2. Synthesis of Salen-Co—X (Salen-Cr—Cl, Salen-Zn, Salen-Cu):

1) Synthesis of Salen-Co—X:

Synthesis of Salen-Co: To a solution of the Salen in toluene under argon was added a solution of $Co(OAc)_2$ in $CH_3OH$ via a syringe, affording a dark red reaction mixture. It was heated to 80~100° C., stirred and refluxed for 4~5 hours. Then the reaction mixture was cooled down to room temperature and concentrated, and the afforded residue was dissolved in $CH_2Cl_2$ and filtered through celite. Removing solvent of the filtrate afforded a dark red powder Salen-Co;

Synthesis of Salen-Co—X: To a solution of the Salen-Co in toluene and $CH_2Cl_2$ (volume ratio of toluene and $CH_2Cl_2$=1:3) was added $CH_3COOH$(HCl or HBr or HI) under argon via a syringe. The solution quickly changed from red to brown. After stirring at 25° C. for 4~5 hours, all solvents and excess acid were removed at reduced pressure, affording brown powder Salen-Co—X.

2) Synthesis of Salen-Cr—Cl:

THF was added to a mixture of Salen and $CrCl_2$ via a syringe under argon. The reaction mixture was stirred at 25° C. for 24 hours. The reaction mixture then was stirred under air at ambient temperature for an additional 24 hours. After the reaction mixture was poured into diethyl ether, the organic layer was washed with aqueous saturated $NH_4Cl$ and brine in turn. After filtration, the organic layer was collected yielding a brown powder Salen-Cr—Cl.

3) Synthesis of Salen-Zn:

THF was added to a mixture of Salen and $Et_2Zn$ via a syringe under argon. The reaction mixture was stirred at 25° C. for 24 hours. The crude product was isolated from the concentrated reaction mixture by removal of the solvent under reduced pressure. A pure product Salen-Zn was obtained after recrystallization using THF and water.

4) Synthesis of Salen-Cu:

Anhydrous ethanol was added to a mixture of Salen and $Cu(OAc)_2$ under argon via a syringe. The reaction mixture was stirred at 80° C. for 24 hours. The solvent was removed under reduced pressure, yielding a dark green powder Salen-Cu.

3. Synthesis of CMP

1) Synthesis of CMP-1:

A mixture of toluene and triethylamine (volume ratio of toluene and triethylamine=3:1) was added to a mixture of salen-Co—X, alkynyl benzene A (mole ratio of Salen-Co—X and alkynyl benzene A=1:2~3), copper (I) iodide and tetrakis-(triphenylphosphine)palladium(0) under argon via a syringe. The reaction mixture was heated to 40° C. and stirred for 40 min~1 hour. Then, the reaction mixture was heated to 80~100° C. and refluxed for 72~96 hours. The mixture was cooled to room temperature and the insoluble precipitated polymer was filtered and washed with dichloromethane, methanol, water, and acetone in turn. Further purification of the polymer was carried out by Soxhlet extraction with methanol and dichloromethane (volume ratio=1:1) for 24~36 hours. The product CMP-1 was dried in vacuum for 24 hours at 70° C.

2) Synthesis of CMP-2:

A mixture of toluene and triethylamine (volume ratio of toluene and triethylamine=3:1) was added to a mixture of salen-Cr—Cl, alkynyl benzene A (mole ratio of Salen-Cr—Cl and alkynyl benzene A=1:2~3), copper (I) iodide and tetrakis-(triphenylphosphine)palladium(0) via a syringe under argon. The reaction mixture was heated to 40° C. and stirred for 40 min~1 hour. Then, the reaction mixture was heated to 80~100° C. and refluxed for 72~96 hours. The mixture was cooled to room temperature and the insoluble precipitated polymer was filtered and washed with dichloromethane, methanol, water, and acetone in men. Further purification of the polymer was carried out by Soxhlet extraction with methanol and dichloromethane (volume ratio=1:1) for 24~36 hours. The product CMP-2 was dried in vacuum for 24 hours at 70° C.

3) Synthesis of CMP-3:

A mixture of toluene and triethylamine (volume ratio of toluene and triethylamine=3:1) was added to a mixture of salen-Zn, alkynyl benzene A (mole ratio of Salen-Zn and alkynyl benzene A=1:1~3), copper (I) iodide and tetrakis-(triphenylphosphine)palladium(0) via a syringe under argon. The reaction mixture was heated to 40° C. and stirred for 40 min~1 hour. Then, the reaction mixture was heated to 80~100° C. and refluxed for 72~96 hours. The mixture was cooled to room temperature and the insoluble precipitated polymer was filtered and washed with dichloromethane, methanol, water, and acetone, in turn. Further purification of the polymer was carried out by Soxhlet extraction with methanol and dichloromethane (volume ratio=1:1) for 24~36 hours. The product CMP-3 was dried in vacuum for 24 hours at 70° C.

4) Synthesis of CMP-4:

A mixture of toluene and triethylamine (volume ratio of toluene and triethylamine=3:1) was added to a mixture of salen-Cu, alkynyl benzene A (mole ratio of Salen-Cu and alkynyl benzene A=1:1~3), copper (I) iodide and tetrakis-(triphenylphosphine)palladium(0) via a syringe under argon. The reaction mixture was heated to 40° C. and stirred for 40 min~1 hour under an argon atmosphere. Then, the reaction mixture was heated to 80~100° C. and refluxed for 72~96 hours. The mixture was cooled to room temperature and the insoluble precipitated polymer was filtered and washed with dichloromethane, methanol, water, and acetone in turn. Further purification of the polymer was carried out by Soxhlet extraction with methanol and dichloromethane (volume ratio=1:1) for 24~36 hours. The product CMP-4 was dried in vacuum for 24 hours at 70° C.

4. Synthesis of CMP-5:

The coordination reaction of the polymer with aluminum was carried out after the polymer was obtained.

1) Synthesis of Salen:

With monohydric alcohol (methanol or ethanol) as a solvent, a mixture solution of $R_1$-substituted salicylaldehyde and 1,2-diaminocyclohexane (mole ratio=1:1~30) was stirred for 1~15 hours at 0~150° C. to afford the Salen compounds;

2) Synthesis of Conjugated Microporous Polymer (CMP):

With tetrakis-(triphenylphosphine)palladium(0) and copper(I) iodide as catalysts, salen and 1,3,5-triethynylbenzene were mixed with a mole ratio of 1:1~5. The reaction mixture was heated to 20~150° C. and stirred for 60~90 hours, yielding the polymer. The mole ratio of the tetrakis-(triphenylphosphine)palladium(0) and 1,3,5-triethynylbenzene was 1:2~50, whereas the mole ratio of copper(I) iodide and 1,3,5-triethynylbenzene was 1:10~40.

3) Synthesis of Aluminum Coordination Catalyst (CMP-5):

The aluminum compound was mixed with the CMP obtained got by the procedure above with a quality ratio of 1:1~6. Then the mixture reacted at 90~130° C. for 8~15 hours, yielding the target CMP-5.

4) Catalyzing the Coupling Reaction of $CO_2$ and Epoxides:

Before sufficient $CO_2$ was introduced, the amine compounds were added to a mixture of the CMP-Al and epoxides in which the mole ratio of the CMP-Al and epoxides was 1:1~25, while the mole ratio of the amine compounds and the epoxides was 1:5~1000. Then the reaction was stirred for 1~80 hours at 0~160° C., affording the cyclic carbonates. The amine compounds mentioned above are quaternary ammonium salts, triethylamine or 4-dimethylamino pyridine.

The structures of the conjugated microporous polymer (CMP) catalysts:

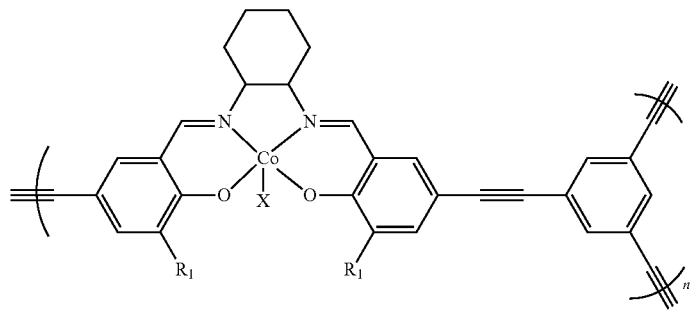

CMP-1-1

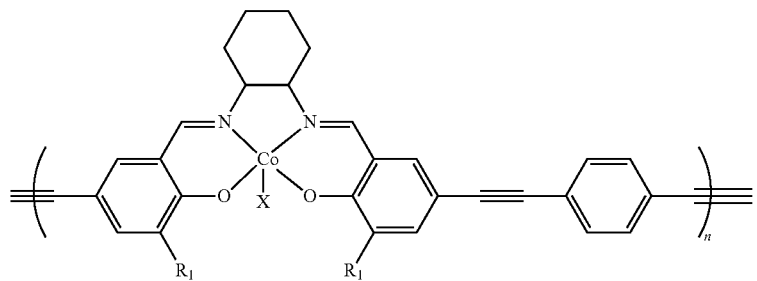

CMP-1-2

-continued
CMP-1-3
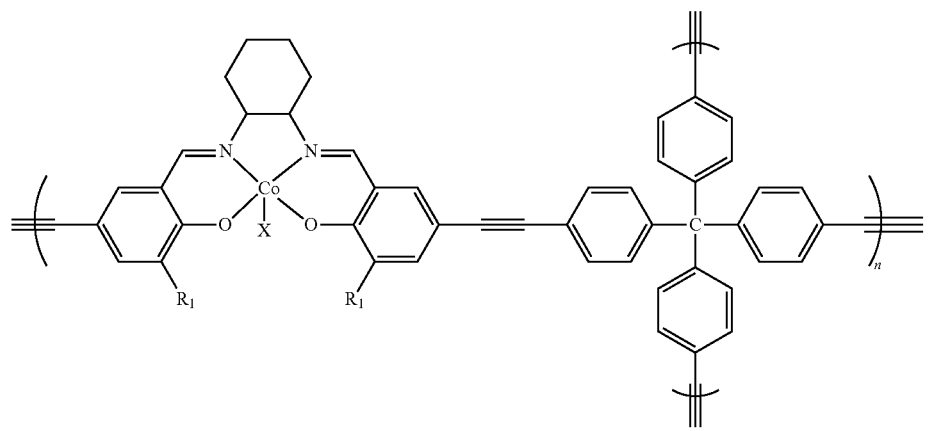
CMP-2-1
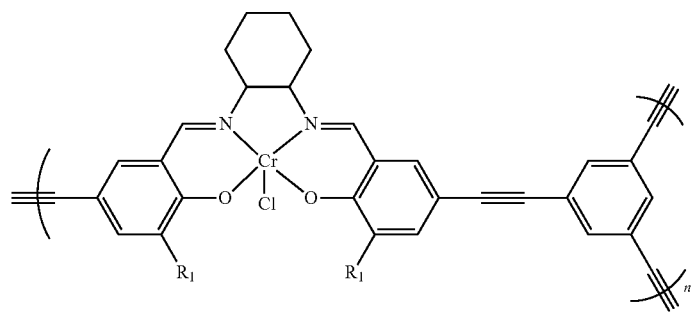
CMP-2-2
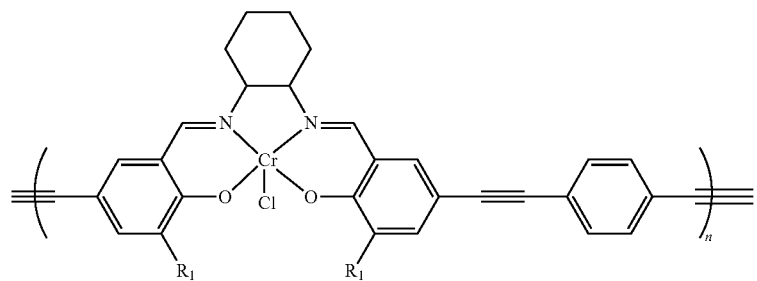
CMP-2-3
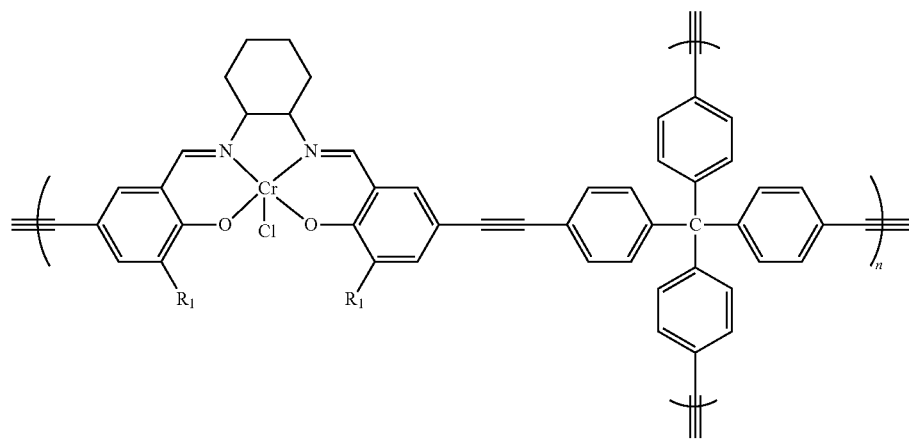

-continued
CMP-3-1
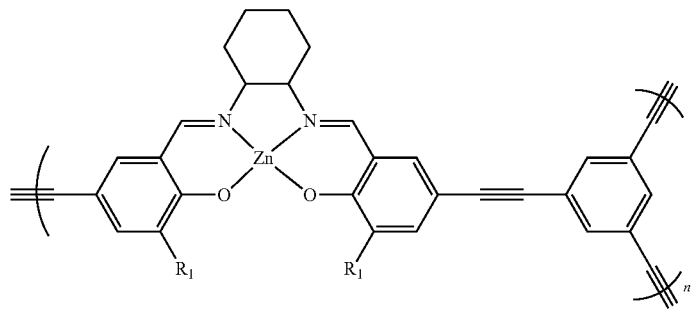
CMP-3-2
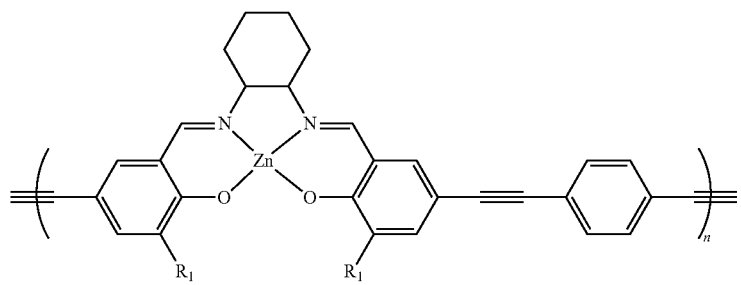
CMP-3-3
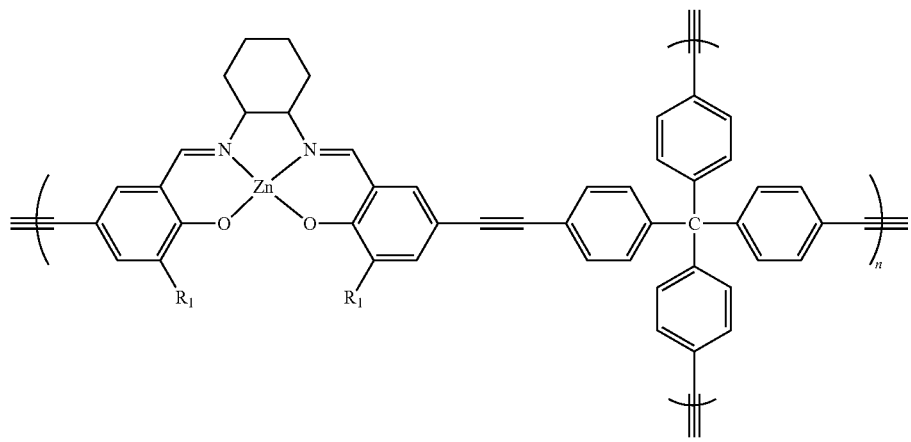
CMP-4-1
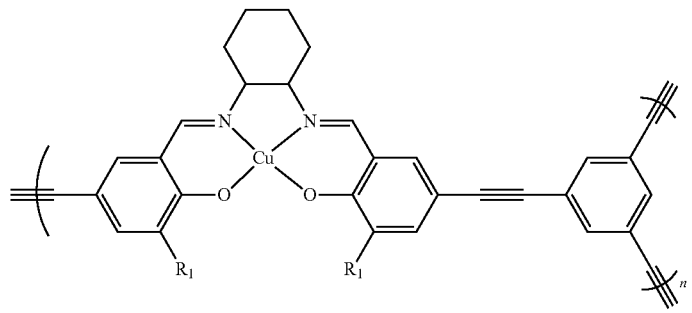
CMP-4-2
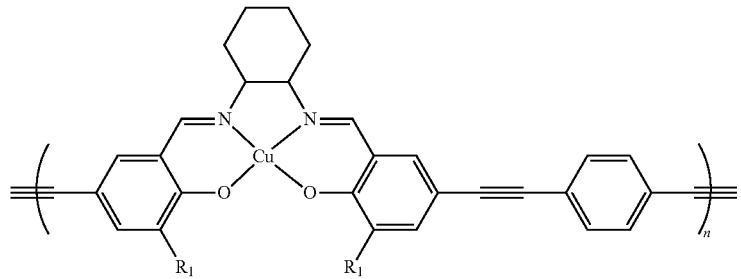

-continued
CMP-4-3
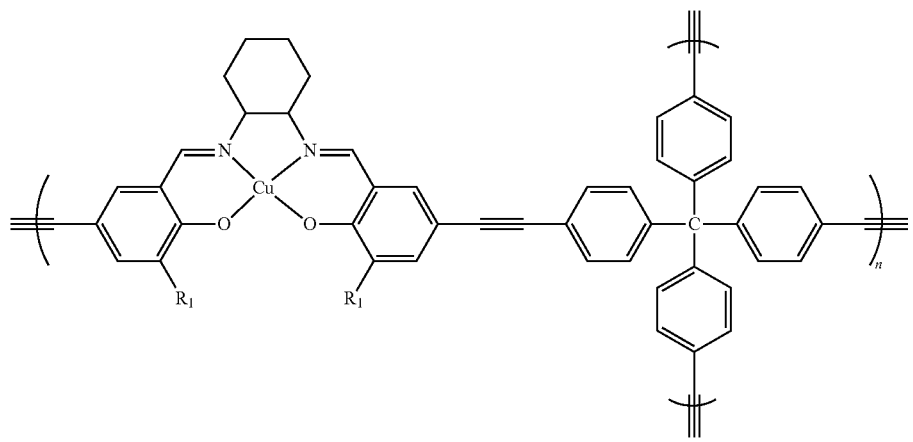
CMP-5-1
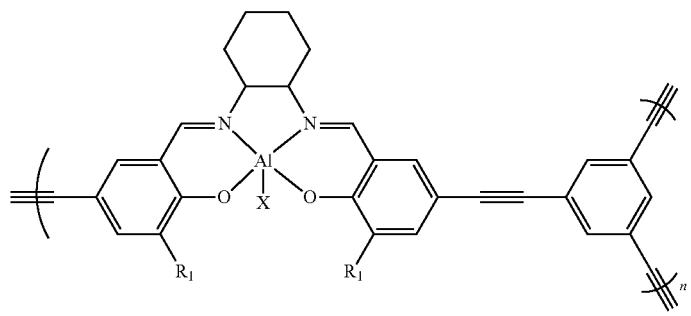
CMP-5-2
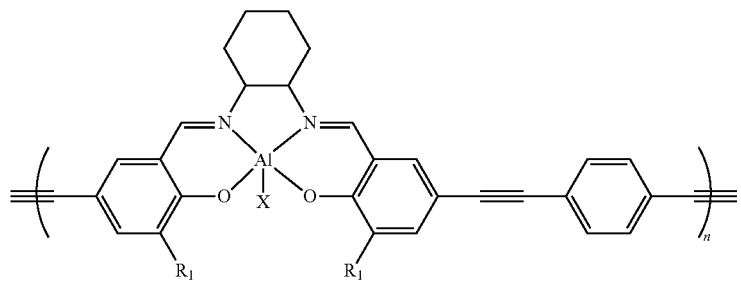
CMP-5-3
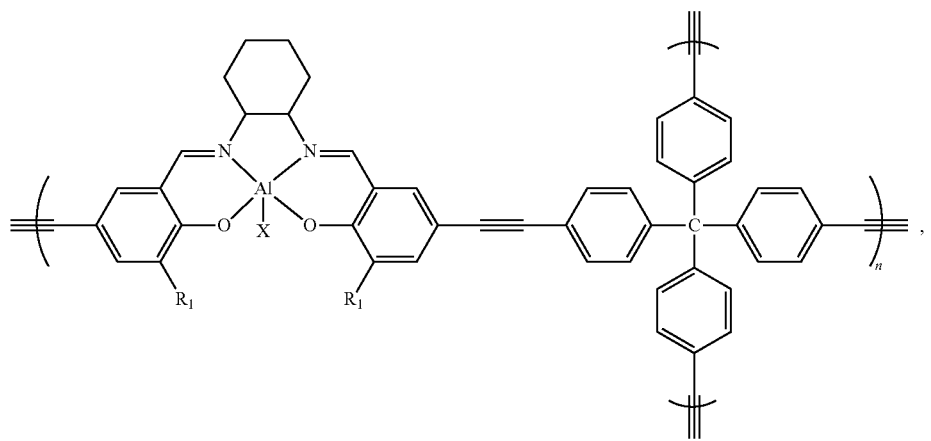

wherein, $R_1$=—H, $-^tBu$, $-^iBu$, —$NO_2$, —Cl, —$CH_2NEt_2$, —$CH_2N(Bn)Et_2Br$, —$CH_2N(CH_3)_2CH_2Ph$,

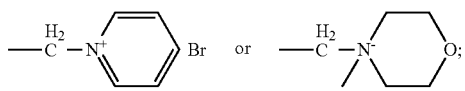

X=—OAc or —Cl or —Br or —I or -Et or —OMe or —OEt or —$OCH_2CH_2(OCH_2CH)_2Cl$. Degree of polymerization for synthesized conjugated polymer compound is in the range of 30~100. These stereochemical structures of the polymer catalysts are consisting of three-dimensional crosslinking networks. The chemical conversion of $CO_2$ with terminal epoxides to form corresponding cyclic carbonates under the CMP-1~5 polymer catalyst system above was achieved in excellent yields (35~90%) of corresponding cyclic carbonate at mild conditions. And the catalyst could be reused without reducing the yields. Simultaneously, holding the reaction condition in the range of 50~180° C. for the reaction temperature and 2~8 MPa for the pressure of $CO_2$, the yields can be up to 90% above while the reaction time only takes 1~3 hours (excluding the CMP-4).

To prepare CMP-1~5, the dibromo-functionalized precursor monomers Salen-Co, Salen-Cr—Cl, Salen-Zn, Salen-Cu were first synthesized by complexation reaction of metal salt [$Co(OAc)_2$, $CrCl_2$, $Et_2Zn$, $Cu(OAc)_2$] and Salen. The resulted precursors were polymerized with alkynyl benzene (A) to produce corresponding conjugated microporous polymers (excluding the CMP-5). The polymers generated by the procedure can adsorb $CO_2$ molecules, increasing the solubility of $CO_2$ in solvent, which leads to the improvement of the reaction yields with recycling ability. Simultaneously, the catalysts can obviously shorten the reaction time for catalyzing the reaction of $CO_2$ and epoxides at high temperatures and high pressures.

Synthetic Routes for the Polymers (CMP-1, CMP-2, CMP-3, CMP-4):

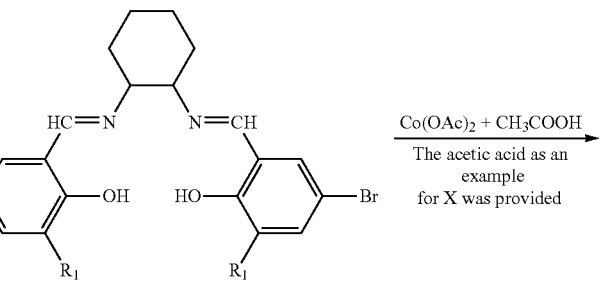

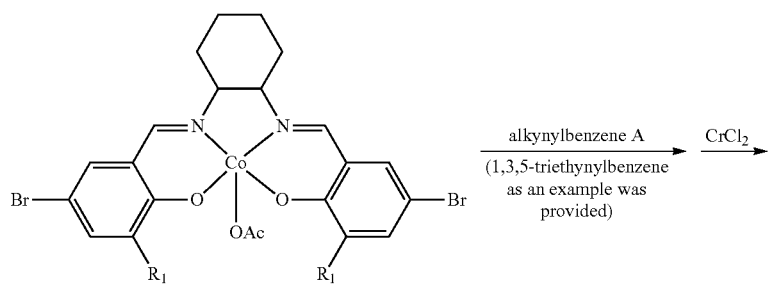

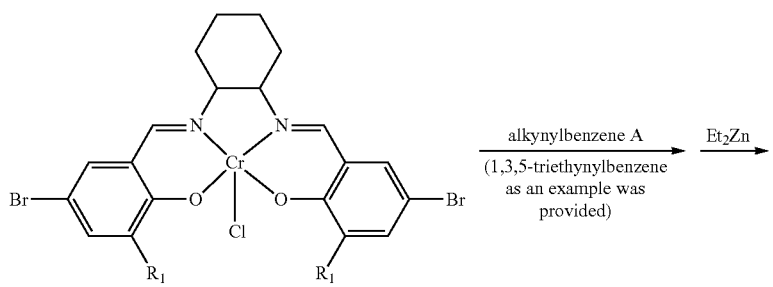

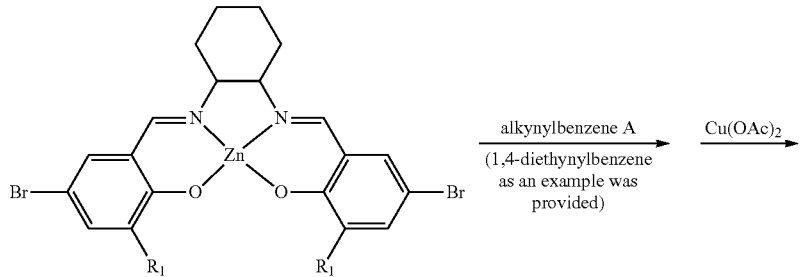

-continued
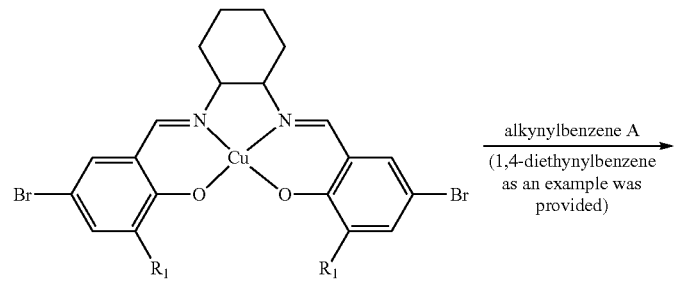 alkynylbenzene A
(1,4-diethynylbenzene
as an example was
provided)
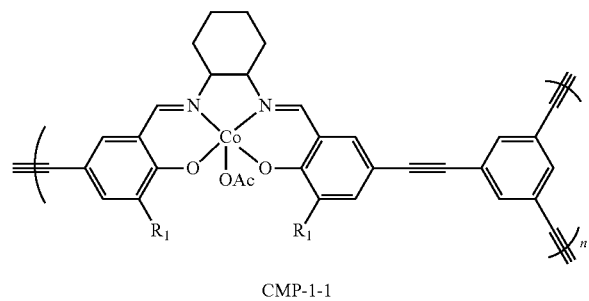
CMP-1-1
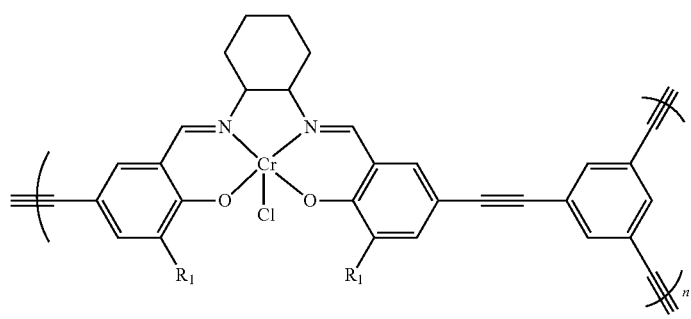
CMP-2-1
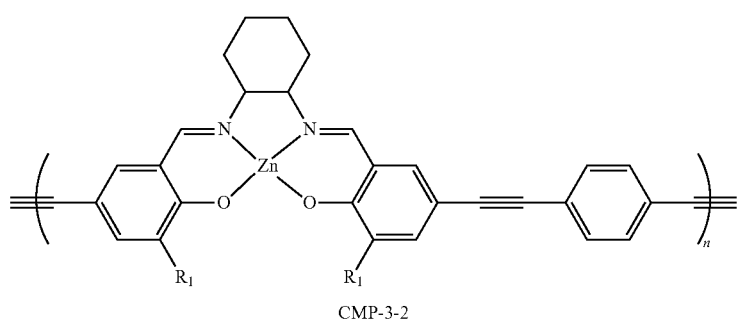
CMP-3-2
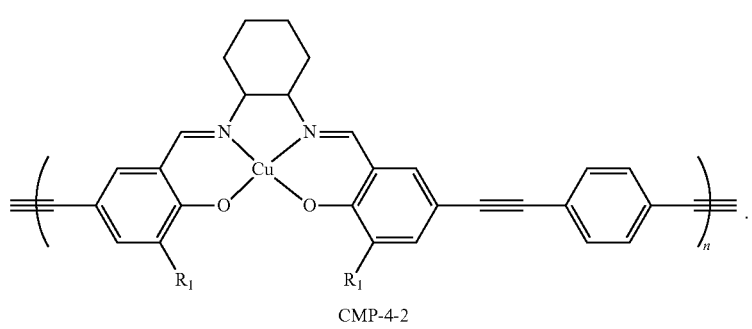
CMP-4-2

Synthetic Routes for CMP-5:

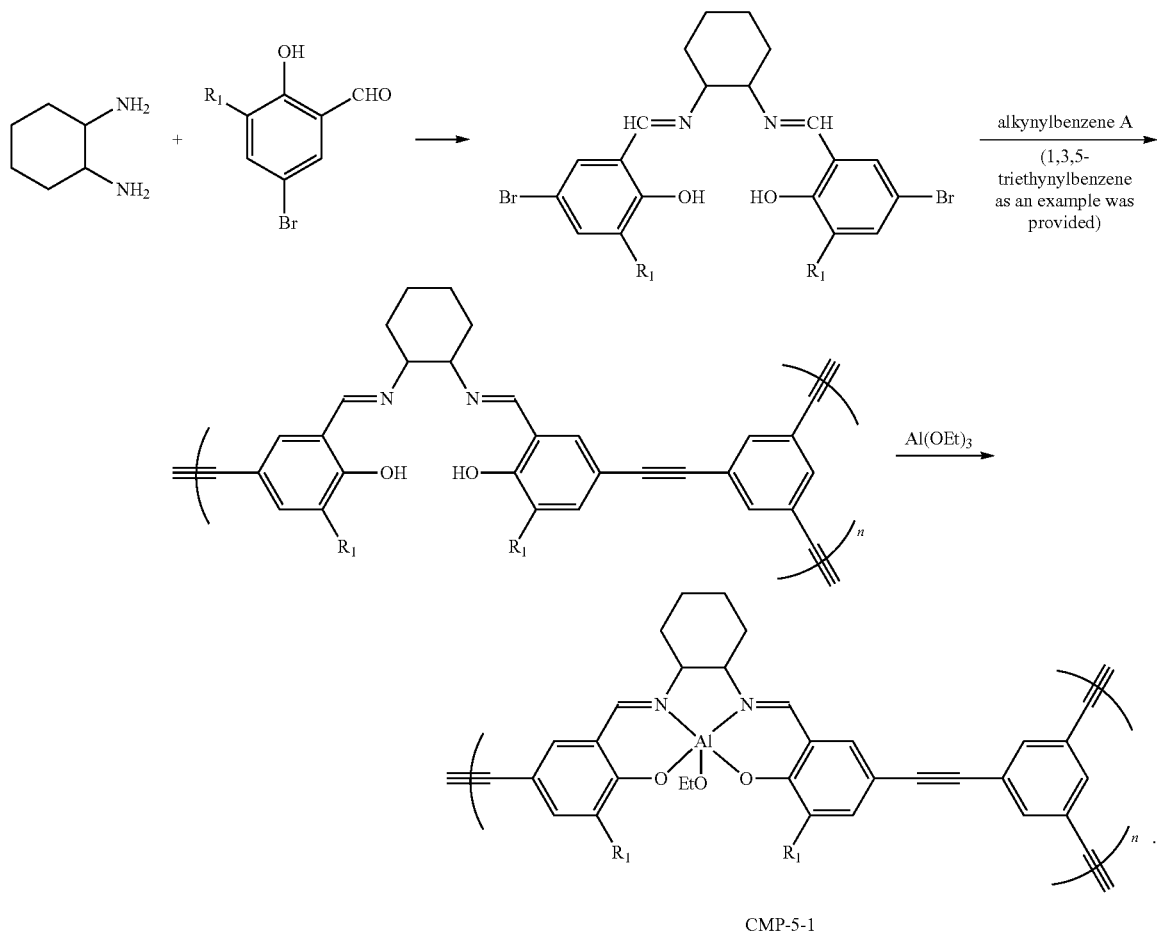

CMP-5-1

The coupling of epoxides and $CO_2$ by polymer catalyst (CMP):

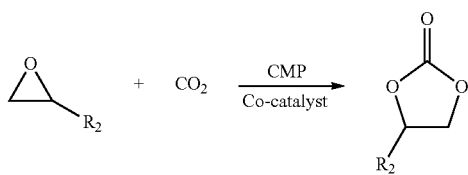

CMP: CMP-1, CMP-2, CMP-3, CMP-4 or CMP-5; Co-catalyst: quaternary ammonium salts (Tetrabutyl ammonium bromide and tetrabutyl ammonium chloride and tetrabutyl ammonium acetate), TEA, DMAP; $R_2$=-Me, —$C_2H_5$, -Ph, —$CH_2$Ph, -Bu or —$C_8H_{17}$. The amount of substance ratio for epoxides, CMP and Co-catalyst is about 200~2000:1:1.

In this invention, a series of new metal-conjugated microporous polymer catalysts were synthesized and used to catalyze the reaction of epoxides and $CO_2$ to produce corresponding cyclic carbonates at ambient pressures and temperatures. The procedure is a breakthrough for overcoming the limitation of this reaction which can only occur at high pressure of $CO_2$ and temperature catalyzed by other catalysts. The yields of cyclic carbonates were in the range of 30~90% at ambient pressures and temperatures. Remarkably, the polymer catalyst can be reused for many times without reducing the yields. Besides, elevating the pressure and the temperature can shorten the reaction time to 1~6 hours, with the yields above 90%.

DETAILED DESCRIPTION OF THE PRESENTLY PREFERRED EMBODIMENTS

The technological invention embodiment is not limited in the specific examples below, including the any combination of these detailed implementation programs.

Example 1

Figure 2:
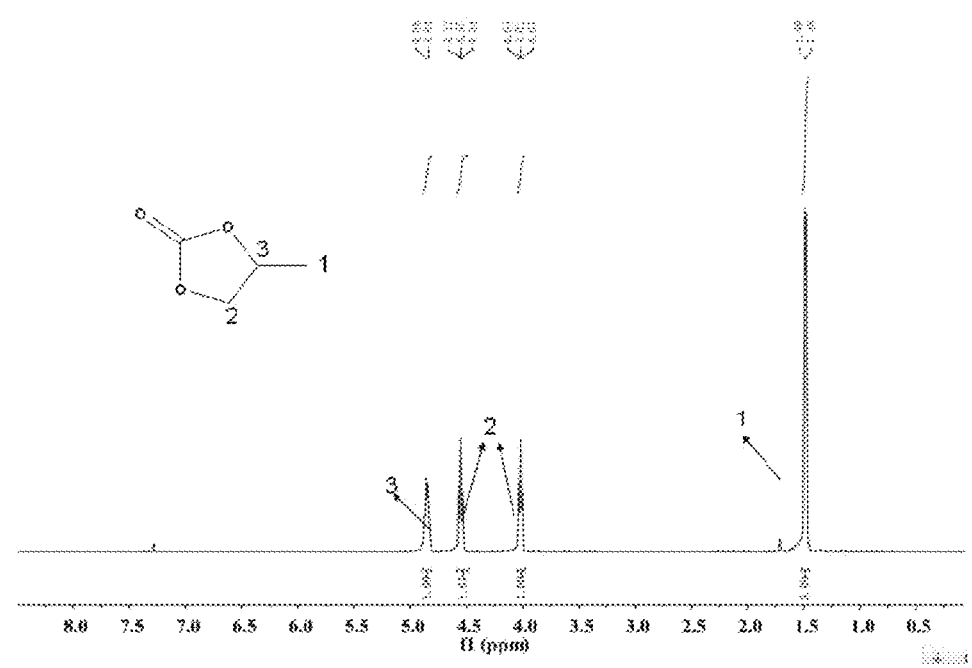
FIG. 2: $^1$H NMR of the 4-Methyl-[1,3]dioxolan-2-one ($CDCl_3$, measured under 400 MHz NMR equipment)

1. Synthesis of Salen-Co:

A solution of Co(OAc)$_2$ (1 mmol) in CH$_3$OH (10 ml) was added to a solution of the Salen (0.75 mmol) in 10 mL anhydrous toluene (10 ml) via a syringe. The reaction mixture was refluxed for 5 hours at 80° C., yielding the target Salen-Co;

2. Synthesis of Salen-Co—OAc:

The acetic acid (6.5 mmol) was added to a solution of the Salen-Co (0.65 mmol) in toluene (6 ml) and CH$_2$Cl$_2$ (18 ml) via a syringe under argon. The mixture was stirred for 5 hours at 25° C., yielding the target Salen-Co—OAc, and its NMR spectrum was shown in FIG. 2.

Figure 12:
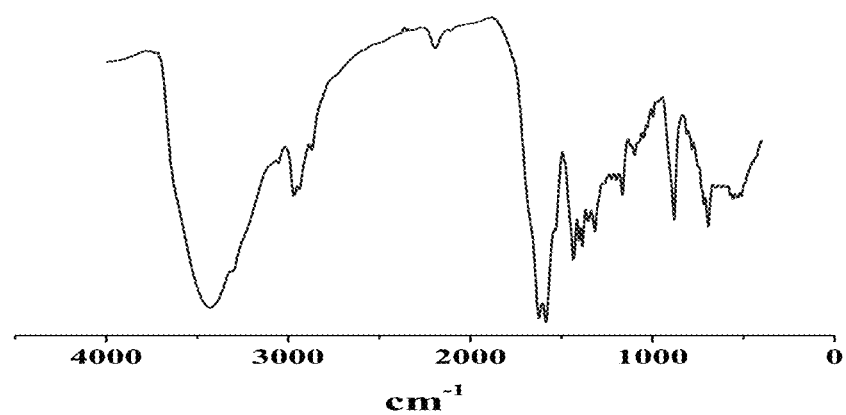
FIG. 12: The FT-IR spectra of CMP-1-1.
Figure 17:
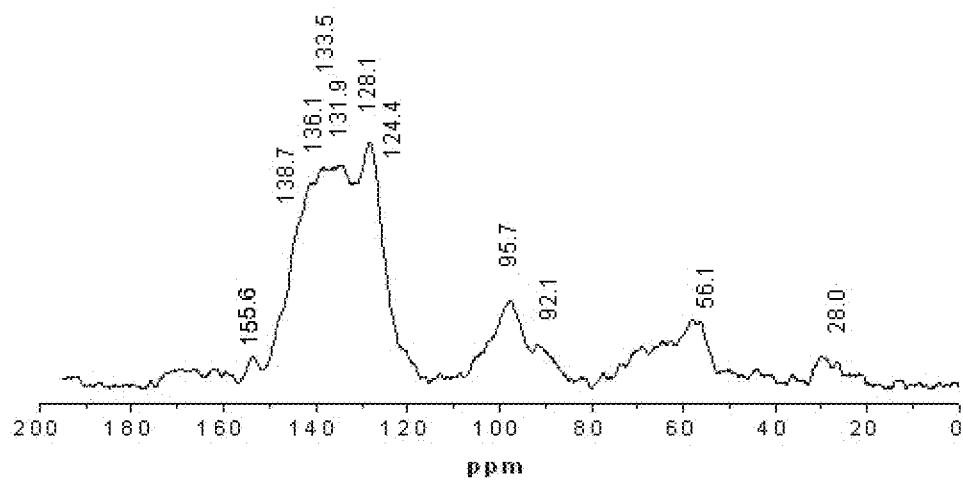
FIG. 17: Solid-state NMR spectra for the CMP-1-1.

3. Synthesis of CMP-1-1:

Salen-Co—OAc (0.45 mmol), 1,3,5-triethynylbenzene (1.35 mmol), copper(I) iodide (40 mg) and tetrakis-(triphenylphosphine)palladium(0) (80 mg) were dissolved in a mixture of toluene (15 ml) and triethylamine (5 ml). Then the reaction mixture was refluxed at 85° C. for 72 hours. After post-processing, CMP-1-1 was obtained. The FT-IR spectra and the Solid-state NMR spectra of the CMP-1-1 were shown in FIG. 12 and FIG. 17, respectively.

Figure 3:
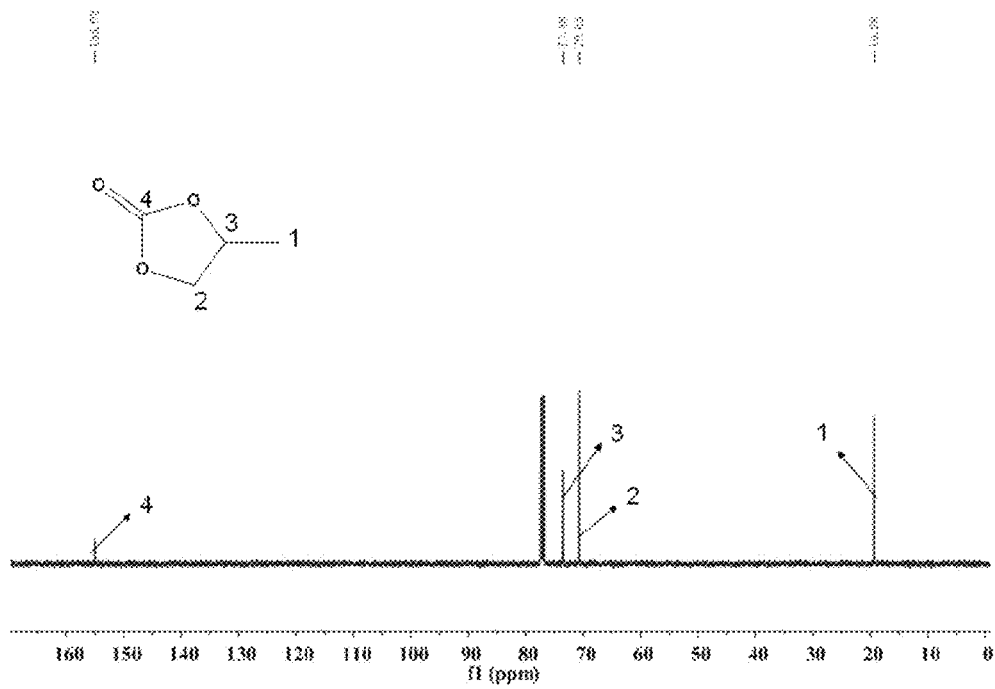
FIG. 3: $^{13}$C NMR of the 4-Methyl-[1,3]dioxolan-2-one ($CDCl_3$, measured under 400 MHz NMR equipment)
Figure 4:
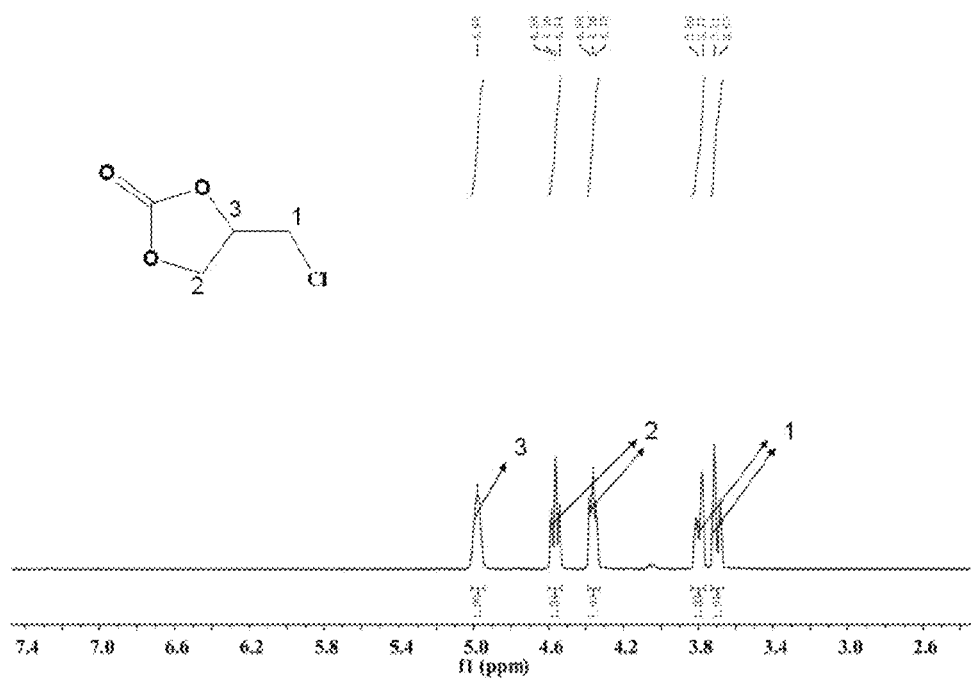
FIG. 4: $^1$H NMR of the 4-Choloro-[1,3]dioxolan-2-one ($CDCl_3$, measured under 400 MHz NMR equipment)

4. Catalyzing for the Coupling Reaction of CO$_2$ and Epoxides:

1) A mixture of 100 mg CMP-1-1, 600 mg TBAB and 1.75 ml propylene oxide was stirred for 48 hours at ambient pressure and temperature, and the yield of the propylene carbonate is 87.5%;

2) With 3.0 MPa CO$_2$ introduced, a mixture of 100 mg CMP-1-1, 600 mg TBAB and 1.75 ml propylene oxide was stirred for 6 hours at 45° C., and the yield of the propylene carbonate is 94.5%. The $^1$H and $^{13}$C NMR for the propylene carbonate were shown in FIG. 3 and FIG. 4.

Example 2

1. Synthesis of Salen-Co:

A solution of Co(OAc)$_2$ (1 mmol) in CH$_3$OH (10 ml) was added to a solution of the Salen (0.6 mmol) anhydrous toluene (10 ml) via a syringe. Then the reaction mixture was refluxed for 5 hours at 80° C., yielding the target Salen-Co;

2. Synthesis of Salen-Co—OAc:

The acetic acid (5 mmol) was added to a solution of the Salen-Co (0.5 mmol) in toluene (5 ml) and CH$_2$Cl$_2$ (15 ml) via a syringe under argon. Then the mixture was stirred for 5 hours at 25° C., yielding the target Salen-Co—OAc, and the NMR spectrum was shown in FIG. 2.

3. Synthesis of CMP-1-1:

Salen-Co—OAc (0.6 mmol), 1,3,5-triethynylbenzene (2.4 mmol), copper(I) iodide (60 mg) and tetrakis-(triphenylphosphine)palladium(0) (100 mg) were dissolved in a mixture of toluene (16 ml) and triethylamine (6 ml). Then the reaction mixture was refluxed at 85° C. for 72 hours. After post-processing, CMP-1-1 was obtained. The FT-IR spectra and the Solid-state NMR spectra of the CMP-1-1 were shown in FIG. 12 and FIG. 17, respectively.

4. Catalyzing the Coupling Reaction of CO$_2$ and Epoxides:

1) A mixture of 100 mg CMP-1-1, 400 mg TBAB and 1.75 ml propylene oxide was stirred for 48 hours at ambient pressure and temperature, and the yield of the propylene carbonate is 80.5%;

2) With 3.0 MPa CO$_2$ introduced, a mixture of 100 mg CMP-1-1, 600 mg TBAB and 1.75 ml propylene oxide was stirred for 4 hours at 60° C., and the yield of the propylene carbonate is 98.5%. The $^1$H and $^{13}$C NMR for the propylene carbonate were shown in FIG. 3 and FIG. 4;

3) A mixture of 100 mg CMP-1-1, 200 mg TBAB and 1.75 ml propylene oxide was stirred for 48 hours in CO$_2$ at the ambient pressure and temperature, and the yield of the propylene carbonate is 56.5%;

4) With 5.0 MPa CO$_2$ introduced, a mixture of 100 mg CMP-1-1, 600 mg TBAB and 1.75 ml propylene oxide was stirred for 12 hours at 30° C., and the yield of the propylene carbonate is 94.0%. The $^1$H and $^{13}$C NMR for the propylene carbonate were shown in FIG. 3 and FIG. 4.

Example 3

1. Synthesis of Salen-Co:

A solution of Co(OAc)$_2$ (1 mmol) in CH$_3$OH (8 ml) was added to a solution of the Salen (0.5 mmol) in 8 mL anhydrous toluene (10 ml) via a syringe. The reaction mixture was refluxed for 5 hours at 80° C., yielding the target Salen-Co;

2. Synthesis of Salen-Co—OAc:

The acetic acid (9 mmol) was added to a solution of Salen-Co (0.65 mmol) in toluene (5 ml) and CH$_2$Cl$_2$ (15 ml) via a syringe under argon. The mixture was stirred for 6 hours at 25° C., yielding the target Salen-Co—OAc, and the NMR spectrum was shown in FIG. 2.

3. Synthesis of CMP-1-1:

Salen-Co—OAc (0.6 mmol), 1,3,5-triethynylbenzene (2.0 mmol), copper(I) iodide (50 mg) and tetrakis-(triphenylphosphine)palladium(0) (100 mg) were dissolved in a mixture of toluene (16 ml) and triethylamine (5 ml). Then the reaction mixture was refluxed at 85° C. for 72 hours. After post-processing, CMP-1-1 was obtained. The FT-IR spectra and the Solid-state NMR spectra of the CMP-1-1 were shown in FIG. 12 and FIG. 17 respectively.

4. Catalyzing the Coupling Reaction of CO$_2$ and Epoxides:

1) A mixture of 100 mg CMP-1, 400 mg TBAB and 1.75 ml propylene oxide was stirred for 48 hours in CO$_2$ at ambient pressure and temperature, and the yield of the propylene carbonate is 96.5%;

2) With 3.0 MPa CO$_2$ introduced, a mixture of 100 mg CMP-1, 600 mg TBAB and 1.75 ml propylene oxide was stirred for 3 hours at 70° C., and the yield of the propylene carbonate is 97%;

3) A mixture of 100 mg CMP-1, 200 mg TBAB and 1.75 ml propylene oxide was stirred for 48 hours in $CO_2$ at the ambient pressure and temperature, and the yield of the propylene carbonate is 66.5%;

4) With 5.0 MPa $CO_2$ introduced, a mixture of 100 mg CMP-1, 600 mg TBAB and 1.75 ml propylene oxide was stirred for 12 hours at 30° C., and the yield of the propylene carbonate is 94.0%;

5) A mixture of 100 mg CMP-1, 600 mg TBAB and 1.75 ml propylene oxide was stirred for 60 hours in $CO_2$ at ambient pressure and temperature, and the yield of the propylene carbonate is 91.5%;

6) A mixture of 100 mg CMP-1, 600 mg TBAB and 1.75 ml propylene oxide was stirred for 36 hours in $CO_2$ at ambient pressure and temperature, and the yield of the propylene carbonate is 76.5%.

Example 4

1. Synthesis of Salen-Co:

A solution of $Co(OAc)_2$ (1 mmol) in $CH_3OH$ (10 ml) was added to a solution of the Salen (0.6 mmol) in 10 ml anhydrous toluene via a syringe. The reaction mixture was refluxed for 5 hours at 80° C., yielding the target Salen-Co.

2. Synthesis of Salen-Co—OAc:

The acetic acid (5 mmol) was added to a solution of the Salen-Co (0.5 mmol) in toluene (5 ml) and $CH_2Cl_2$ (15 ml) via a syringe under argon. The mixture was stirred for 5 hours at 25° C., yielding the target Salen-Co—OAc, and the NMR spectrum was shown in FIG. 2.

Figure 13:
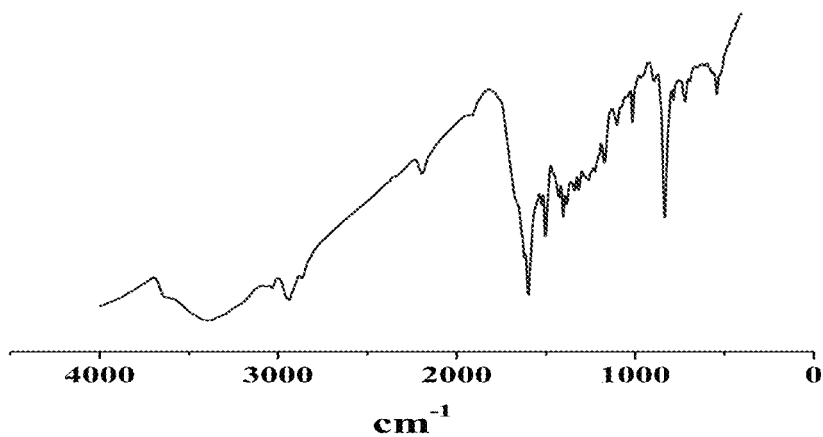
FIG. 13: The FT-IR spectra of CMP-1-2.
Figure 18:
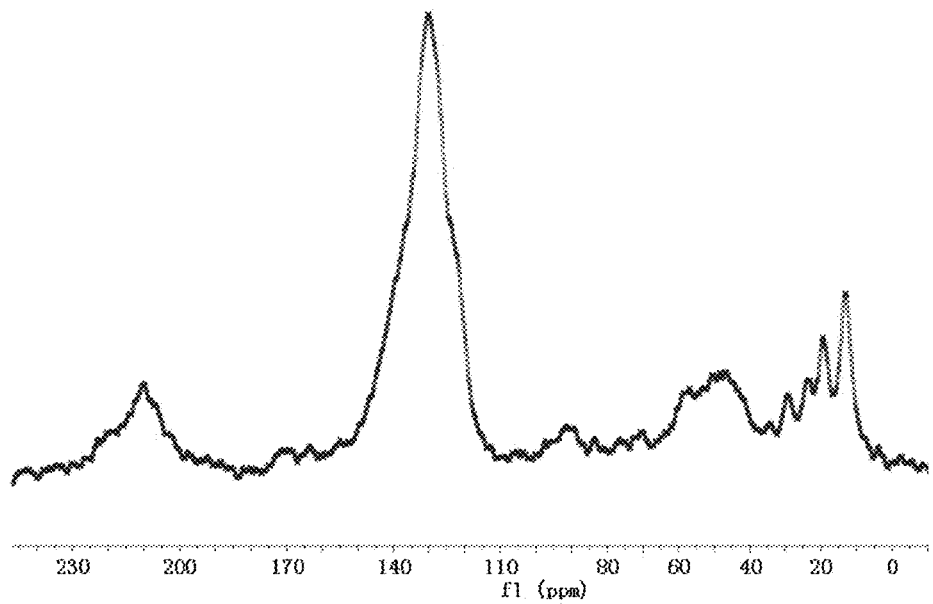
FIG. 18: Solid-state NMR spectra for the CMP-1-2.

3. Synthesis of CMP-1-2:

Salen-Co—OAc (0.6 mmol), 1,4-diacetylenebenzene (1.2 mmol), copper(I) iodide (50 mg) and tetrakis-(triphenylphosphine)palladium(0) (90 mg) were dissolved in a mixture of toluene (16 ml) and triethylamine (6 ml). Then the reaction mixture was refluxed at 85° C. for 72 hours. After post-processing, CMP-1-2 was obtained. The FT-IR spectra and the Solid-state NMR spectra of the CMP-1-2 were shown in FIG. 13 and FIG. 18, respectively.

4. Catalyzing for the Coupling Reaction of $CO_2$ and Epoxides:

1) A mixture of 100 mg CMP-1-2, 600 mg TBAB and 1.75 ml propylene oxide was stirred for 48 hours in $CO_2$ at ambient pressure and temperature, and the yield of the propylene carbonate is 66.5%;

2) With 3.0 MPa $CO_2$ introduced, a mixture of 100 mg CMP-1-2, 600 mg TBAB and 1.75 ml propylene oxide was stirred for 2 hours at 90° C., and the yield of the propylene carbonate is 85.9%;

3) With 100 mg CMP-1-2, 600 mg TBAB and 1.75 ml propylene oxide in the mixture, the reaction mixture was stirred for 24 hours in $CO_2$ at ambient pressure and temperature, and the yield of the propylene carbonate is 52.5%;

4) With 3.0 MPa $CO_2$ introduced, a mixture of 100 mg CMP-1-2, 600 mg TBAB and 1.75 ml propylene oxide was stirred for 2 hours at 110° C., and the yield of the propylene carbonate is 91.1%;

5) With 4.0 MPa $CO_2$ introduced, a mixture of 100 mg CMP-1-2, 600 mg TBAB and 1.75 ml propylene oxide was stirred for 1 hour at 120° C., and the yield of the propylene carbonate is 64.2%. The $^1H$ and $^{13}C$ NMR spectrums for the propylene carbonate were shown in FIG. 3 and FIG. 4.

Example 5

1. Synthesis of Salen-Cr—Cl:

The chromium (II) chloride (0.8 mmol) and Salen (N'N'-bis(3-tert-butyl-5-bromo-salicylidene)-1,2-diaminocyclohexane (0.6 mmol) were dissolved in dried THF (12 mL). The mixture was stirred under argon at 25° C. for 24 hours and for another 24 hours in the air. After that the compound Salen-Cr—Cl was obtained.

Figure 14:
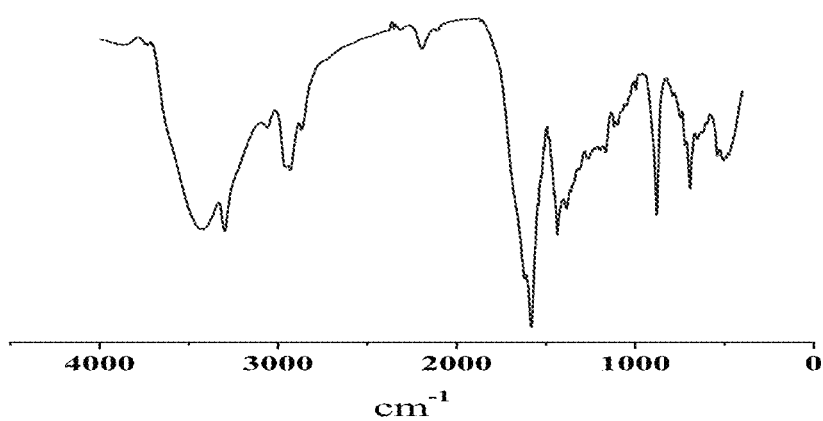
FIG. 14: The FT-IR spectra of CMP-2-1.
Figure 19:
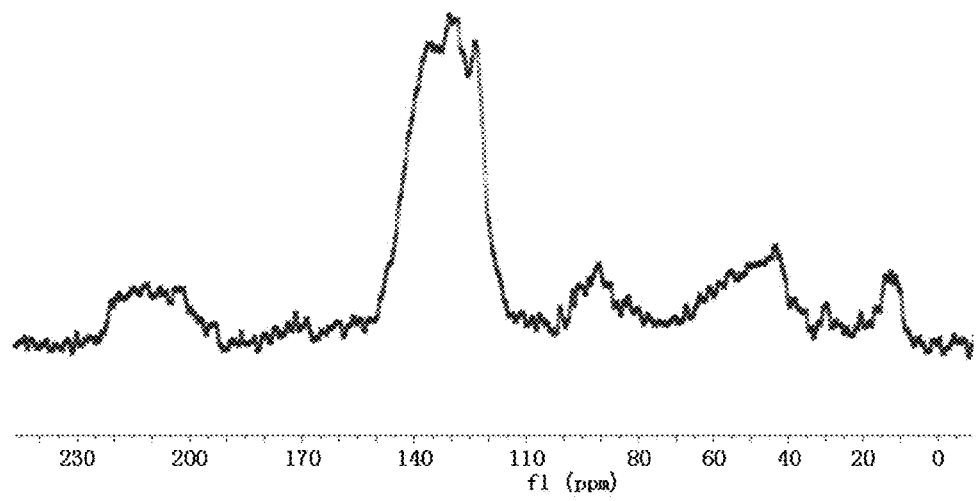
FIG. 19: Solid-state NMR spectra for the CMP-2-1.

2. Synthesis of CMP-2:

1) Synthesis of CMP-2-1: Salen-Cr—Cl (0.4 mmol), 1,3,5-triethynylbenzene (1.2 mmol), copper(I) iodide (40 mg) and tetrakis-(triphenylphosphine)palladium(0) (80 mg) were dissolved in a mixture of toluene (12 ml) and triethylamine (4 ml). The reaction mixture was refluxed at 80° C. for 72 hours, yielding the needed compound CMP-2-1. The FT-IR spectra and the Solid-state NMR spectra of the CMP-2-1 were shown in FIG. 14 and FIG. 19, respectively;

2) Synthesis of CMP-2-2: Salen-Cr—Cl (0.45 mmol), 1,4-diethynylbenzene (1.35 mmol), copper(I) iodide (30 mg) and tetrakis-(triphenylphosphine)palladium(0) (60 mg) were dissolved in a mixture of toluene (15 ml) and triethylamine (5 ml). The reaction mixture was refluxed at 80° C. for 72 hours, yielding the needed compound CMP-2-2;

3) Synthesis of CMP-2-3: Salen-Cr—Cl (0.4 mmol), tetrakis(4-ethynylphenyl)methane (1.2 mmol), copper(I) iodide (40 mg) and tetrakis-(triphenylphosphine)palladium(0) (80 mg) were dissolved in a mixture of toluene (15 ml) and triethylamine (5 ml). The reaction mixture was refluxed at 85° C. for 72 hours, yielding the needed compound CMP-2-3.

Figure 1:
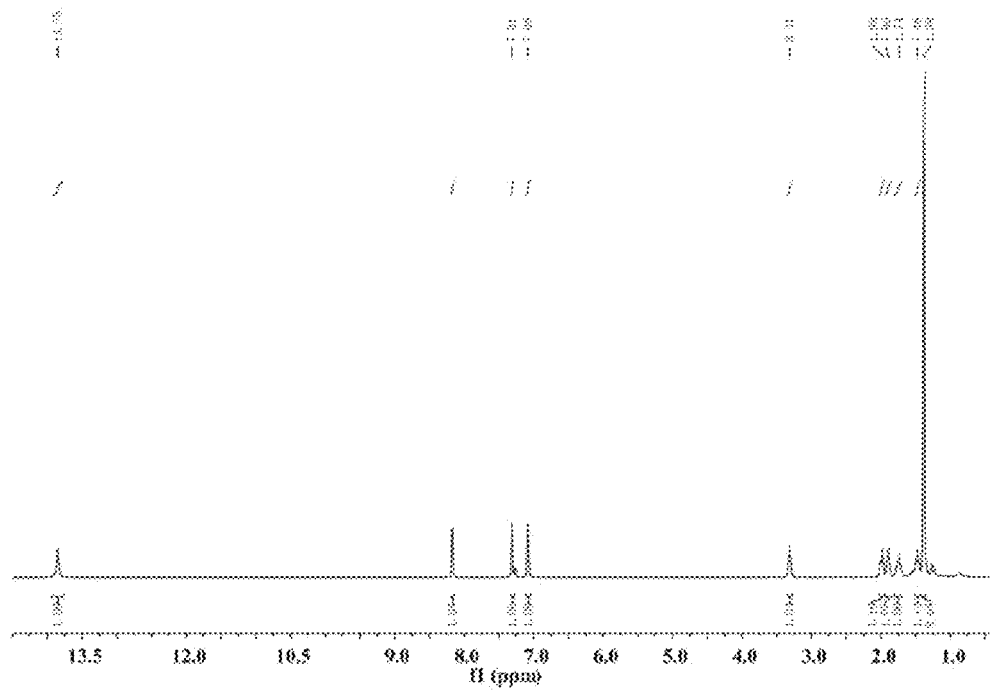
FIG. 1: $^1$H NMR of the Salen [N,N-bis(3-tert-butyl-5-bromo-salicylidene)-1,2-diaminocyclohexane as an example] ($CDCl_3$, measured under 400 MHz NMR equipment)
Figure 5:
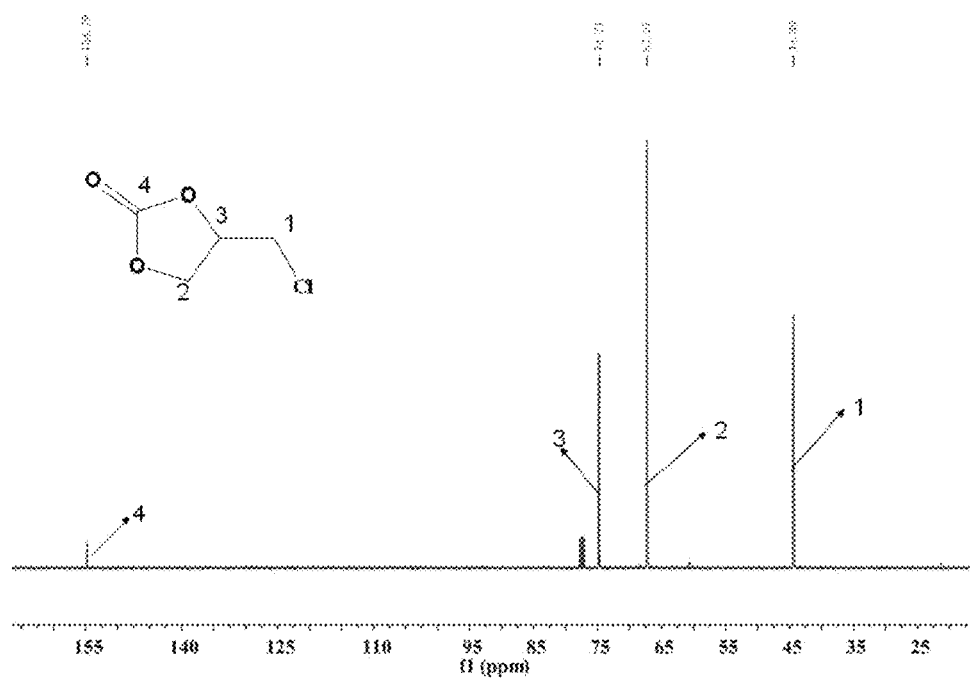
FIG. 5: $^{13}$C NMR of the 4-Choloro-[1,3]dioxolan-2-one ($CDCl_3$, measured under 400 MHz NMR equipment)
Figure 6:
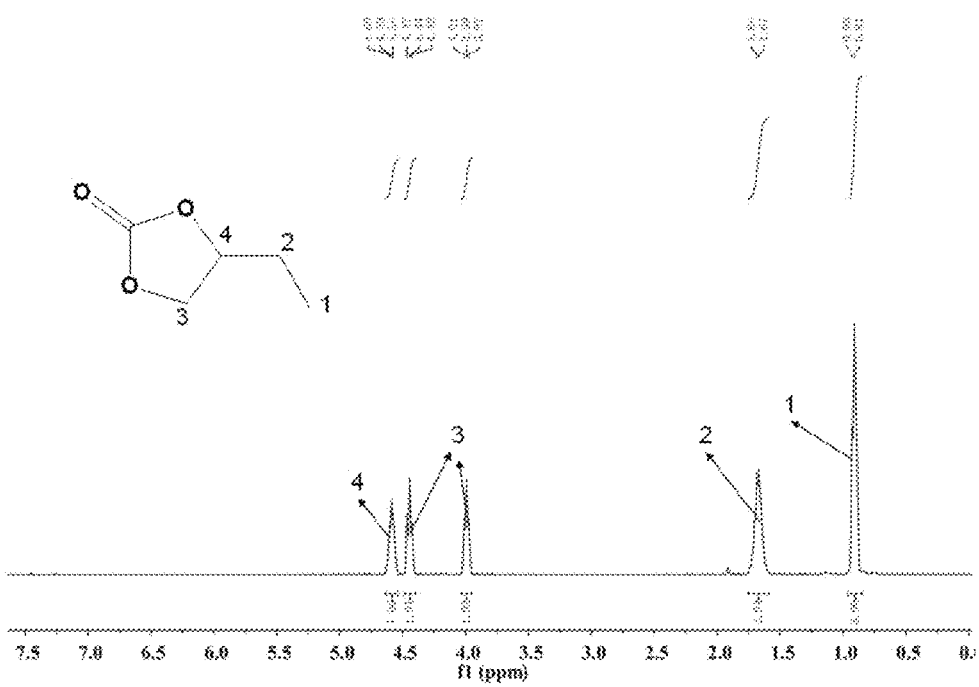
FIG. 6: $^1$H NMR of the 4-Ethyl-[1,3]dioxolan-2-one ($CDCl_3$, measured under 400 MHz NMR equipment)
Figure 7:
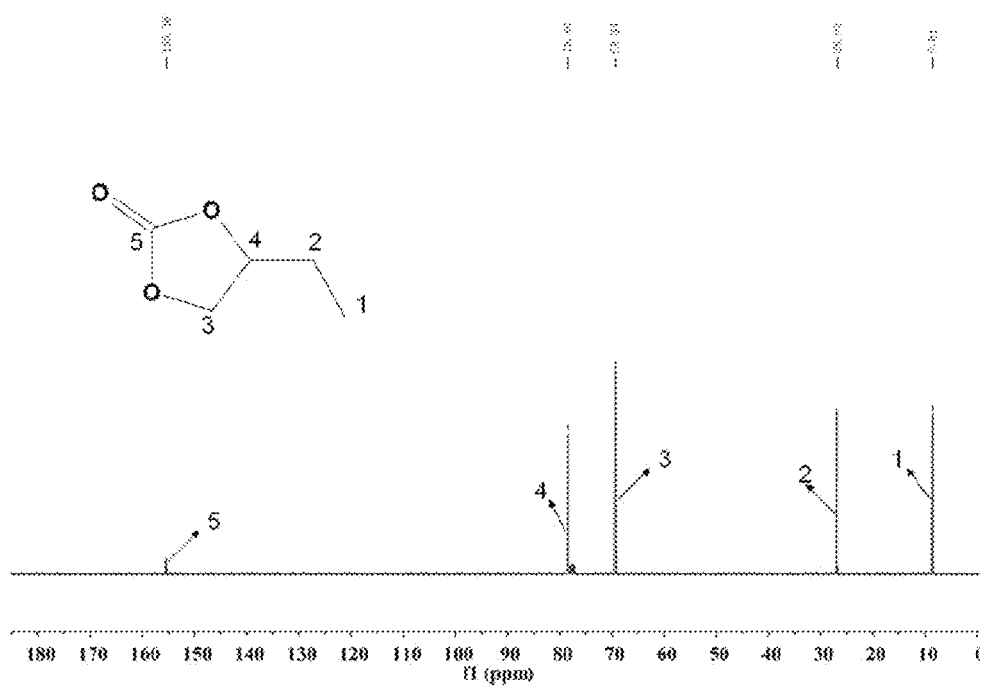
FIG. 7: $^{13}$C NMR of the 4-Ethyl-[1,3]dioxolan-2-one ($CDCl_3$, measured under 400 MHz NMR equipment)
Figure 8:
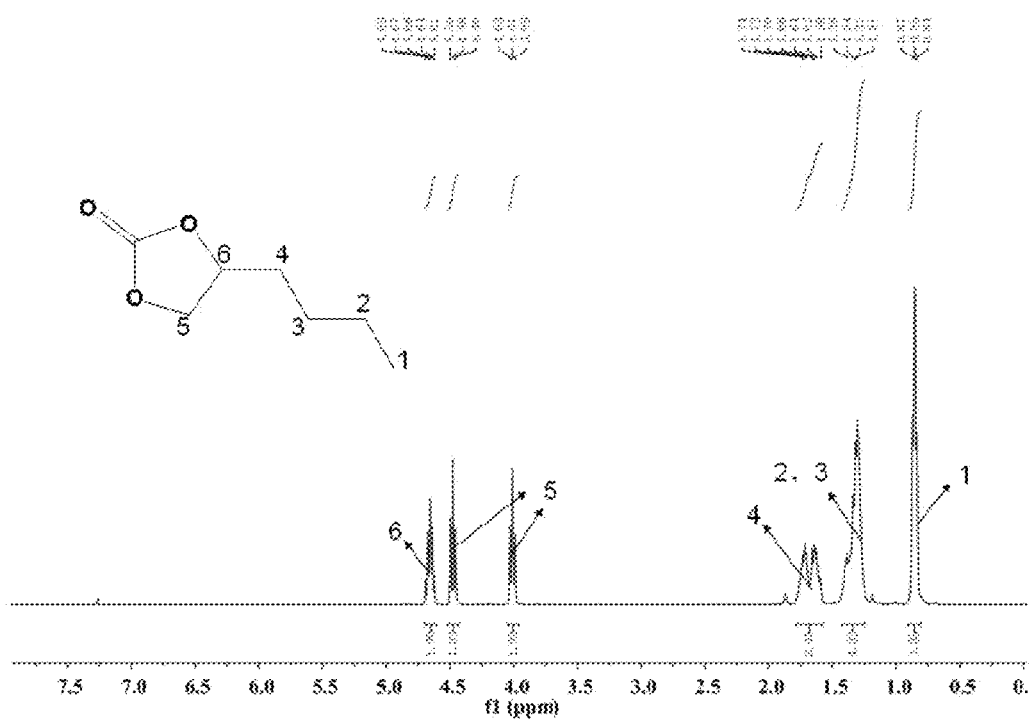
FIG. 8: $^1$H NMR of the 4-Butyl-[1,3]dioxolan-2-one ($CDCl_3$, measured under 400 MHz NMR equipment)
Figure 9:
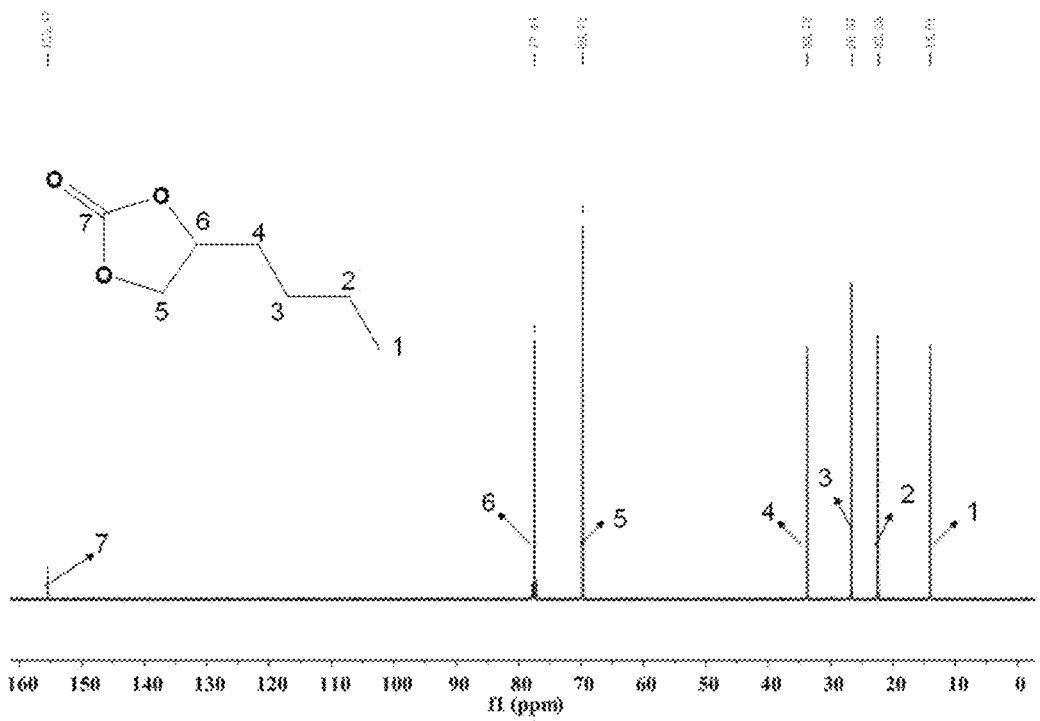
FIG. 9: $^{13}$C NMR of the 4-Butyl-[1,3]dioxolan-2-one (CDCl$_3$, measured under 400 MHz NMR equipment)
Figure 10:
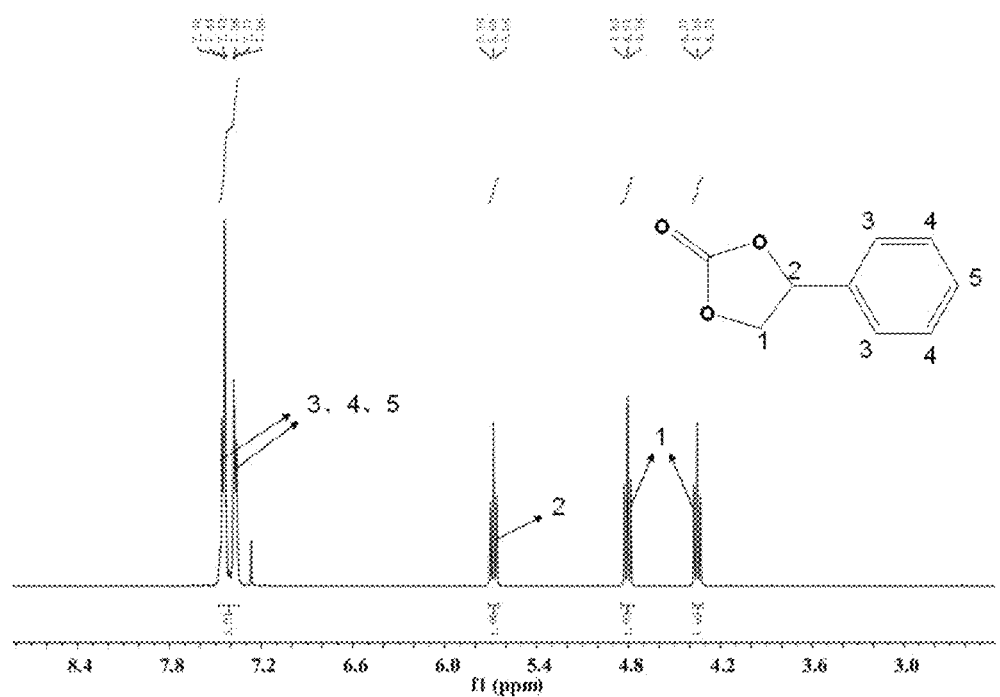
FIG. 10: $^1$H NMR of the 4-Phenyl-[1,3]dioxolan-2-one (CDCl$_3$, measured under 400 MHz NMR equipment)
Figure 11:
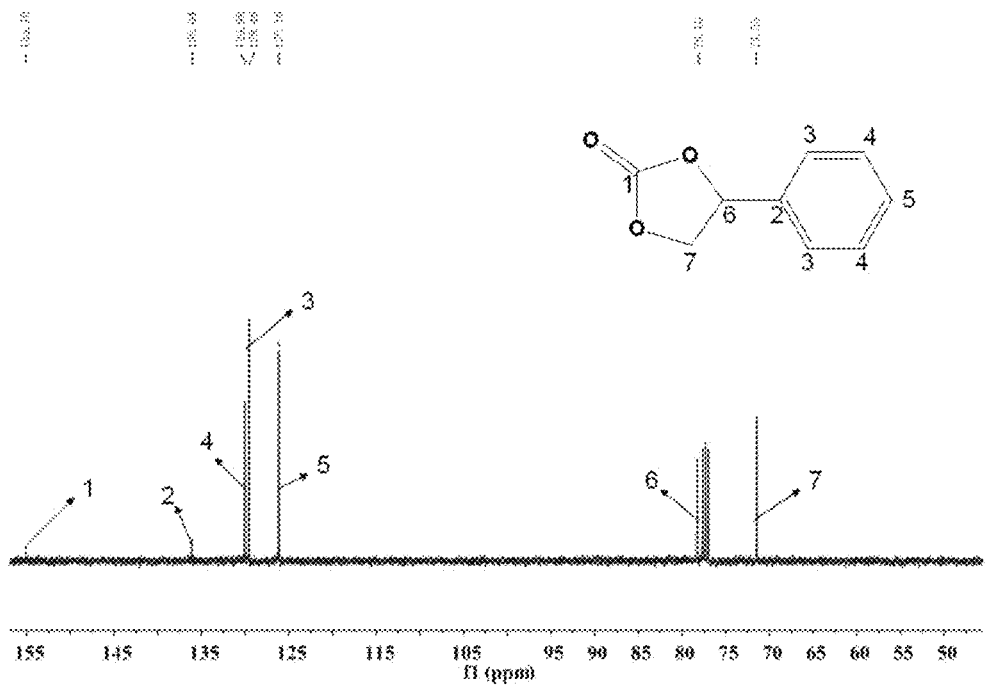
FIG. 11: $^{13}$C NMR of the 4-Phenyl-[1,3]dioxolan-2-one (CDCl$_3$, measured under 400 MHz NMR equipment)

3. Catalyzing for the Coupling Reaction of $CO_2$ and Epoxides:

1) A mixture of 100 mg CMP-2-1, 500 mg TBAB and 1.75 ml propylene oxide was stirred for 48 hours in $CO_2$ at ambient pressure and temperature, and the yield of the propylene carbonate is 67.7%;

2) With 3.0 MPa $CO_2$ introduced, a mixture of 100 mg CMP-2-1, 600 mg TBAB and 1.75 ml propylene oxide was stirred for 1 hour at 100° C., and the yield of the propylene carbonate is 98.5%. The NMR spectrums for the product were shown in FIG. 2 and FIG. 3;

3) With 3.0 MPa $CO_2$ introduced, a mixture of 100 mg CMP-2-1, 600 mg TBAB and 1.96 ml epichlorohydrin was stirred for 1 hour at 100° C., and the yield of the corresponding cyclic carbonate is 99.1%. The NMR spectrums for the product were shown in FIG. 4 and FIG. 5;

4) With 3.0 MPa $CO_2$ introduced, a mixture of 100 mg CMP-2-1, 600 mg TBAB and 2.146 ml 1,2-epoxybutane was stirred for 2 hours at 100° C., and the yield of the corresponding cyclic carbonate is 96.0%. The NMR spectrums for the product were shown in FIG. 6 and FIG. 7;

5) With 3.0 MPa $CO_2$ introduced, a mixture of 100 mg CMP-2-1, 600 mg TBAB and 3.01 ml 1,2-epoxyhexane was stirred for 2 hours at 100° C., and the yield of the corresponding cyclic carbonate is 96.7%. The NMR spectrums for the product were shown in FIG. 8 and FIG. 9;

6) With 3.0 MPa $CO_2$ introduced, a mixture of 100 mg CMP-2-1, 600 mg TBAB and 2.85 ml styrene oxide was stirred for 2 hours at 100° C., and the yield of the corresponding cyclic carbonate is 96.3%. The NMR spectrums for the product were shown in FIG. 10 and FIG. 1;

7) With 3.0 MPa $CO_2$ introduced, a mixture of 100 mg CMP-2-2, 600 mg TBAB and 1.75 ml propylene oxide was stirred for 2 hours at 100° C., and the yield of the corresponding cyclic carbonate is 86.5%.

Example 6

1. Synthesis of Salen-Zn:
The Et$_2$Zn (0.4 ml, 1.0 M in hexane) and Salen (N'N'-bis (3-tert-butyl-5-bromo-salicylidene)-1,2-diaminocyclohexane (0.4 mmol) and were dissolved in dried THF (20 ml). The mixture was stirred under argon at 25° C. for 24 hours. After that the compound Salen-Zn was obtained.

Figure 15:
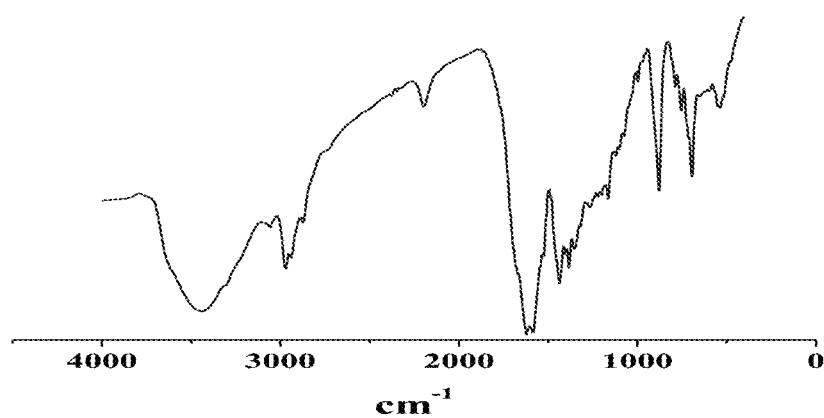
FIG. 15: The FT-IR spectra of CMP-3-1.
Figure 16:
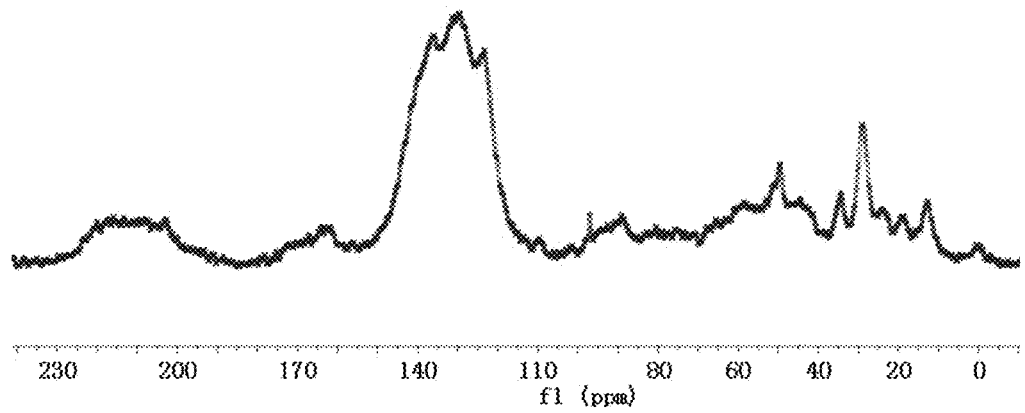
FIG. 16: Solid-state NMR spectra for the CMP-5-1.
Figure 20:
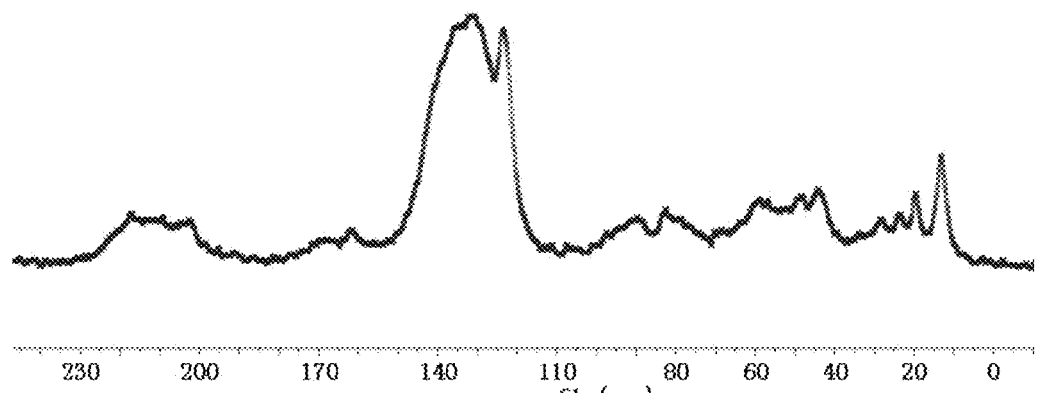
FIG. 20: Solid-state NMR spectra for the CMP-3-1.

2. Synthesis of CMP-3:
1) Synthesis of CMP-3-1: Salen-Zn (0.35 mmol), 1,3,5-triethynylbenzene (1.05 mmol), copper(I) iodide (40 mg) and tetrakis-(triphenylphosphine)palladium(0) (70 mg) were dissolved in a mixture of toluene (12 ml) and triethylamine (4 ml). The reaction mixture was refluxed at 85° C. for 72 hours, yielding the needed compound CMP-3-1. The FT-IR spectra and the Solid-state NMR spectra of the CMP-3-1 were shown in FIG. 15 and FIG. 20, respectively.

2) Synthesis of CMP-3-2: Salen-Zn (0.4 mmol), 1,4-diethynylbenzene (1.2 mmol), copper(I) iodide (35 mg) and tetrakis-(triphenylphosphine)palladium(0) (70 mg) were dissolved in a mixture of toluene (15 ml) and triethylamine (5 ml). The reaction mixture was refluxed at 85° C. for 72 hours, yielding the needed compound CMP-3-2.

3) Synthesis of CMP-3-3: Salen-Zn (0.4 mmol), tetrakis (4-ethynylphenyl)methane (1.2 mmol), copper(I) iodide (40 mg) and tetrakis-(triphenylphosphine)palladium(0) (80 mg) were dissolved in a mixture of toluene (12 ml) and triethylamine (4 ml). The reaction mixture was refluxed at 85° C. for 72 hours, yielding the needed compound CMP-3-3.

3. Catalyzing the Coupling Reaction of $CO_2$ and Epoxides:
1) A mixture of 100 mg CMP-3-1, 500 mg TBAB and 1.75 ml propylene oxide was stirred 48 hours in $CO_2$ at ambient pressure and temperature, and the yield of the propylene carbonate is 85.1%;

2) With 3.0 MPa $CO_2$ introduced, a mixture of 100 mg CMP-3-1, 600 mg TBAB and 1.75 ml propylene oxide was stirred for 2 hours at 100° C., and the yield of the propylene carbonate is 95.2%;

3) With 3.0 MPa $CO_2$ introduced, a mixture of 100 mg CMP-3-1, 600 mg TBAB and 1.96 ml epichlorohydrin was stirred for 2 hours at 100° C., and the yield of the corresponding cyclic carbonate is 99.6%;

4) With 3.0 MPa $CO_2$ introduced, a mixture of 100 mg CMP-3-1, 600 mg TBAB and 2.146 ml 1,2-epoxybutane was stirred for 2 hours at 100° C., and the yield of the corresponding cyclic carbonate is 96.5%;

5) With 3.0 MPa $CO_2$ introduced, a mixture of 100 mg CMP-3-1, 600 mg TBAB and 3.01 ml 1,2-epoxyhexane was stirred for 2 hours at 100° C., and the yield of the corresponding cyclic carbonate is 98.3%;

6) With 3.0 MPa $CO_2$ introduced, a mixture of 100 mg CMP-3-1, 600 mg TBAB and 2.85 ml styrene oxide was stirred for 2 hours at 100° C., and the yield of the corresponding cyclic carbonate is 96.6%;

7) With 3.0 MPa $CO_2$ introduced, a mixture of 100 mg CMP-3-2, 600 mg TBAB and 1.75 ml propylene oxide was stirred for 1 hour at 100° C., and the yield of the corresponding cyclic carbonate is 88.7%.

Example 7

1. Synthesis of Salen-Cu:
The Cu(OAc)$_2$ (0.5 mmol) and Salen (N'N'-bis(3-tert-butyl-5-bromo-salicylidene)-1,2-diaminocyclohexane, 0.5 mmol) and were dissolved in dried ethanol (20 mL). The mixture was stirred at 80° C. for 24 hours. After that the compound Salen-Cu was obtained.

Figure 21:
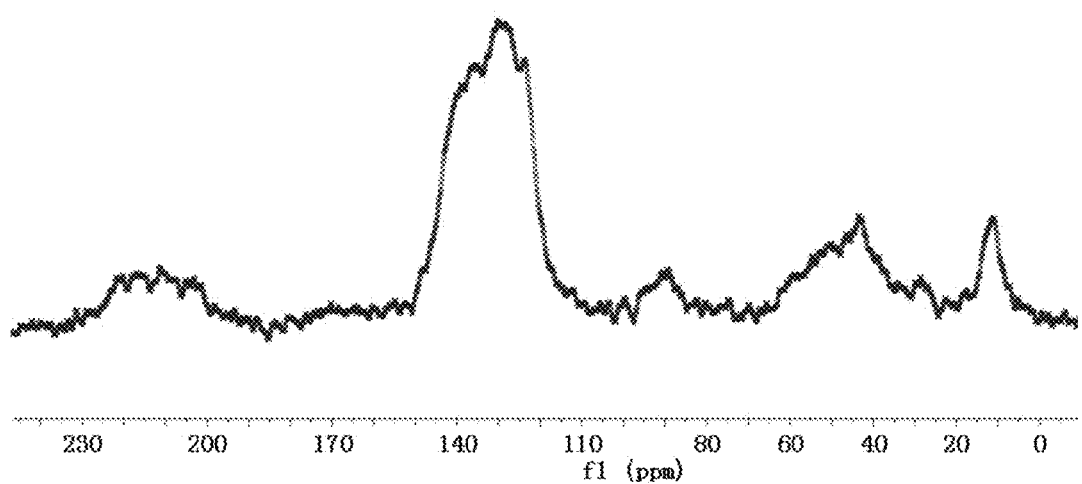
FIG. 21: Solid-state NMR spectra for the CMP-4-1.

2. Synthesis of CMP-4:
1) Synthesis of CMP-4-1: Salen-Cu (0.46 mmol), 1,3,5-triethynylbenzene (1.32 mmol), copper(I) iodide (40 mg) and tetrakis-(triphenylphosphine)palladium(0) (80 mg) were dissolved in a mixture of toluene (15 ml) and triethylamine (5 ml). The reaction mixture was refluxed at 80° C. for 72 hours, yielding the needed compound CMP-4-1. The Solid-state NMR spectra of the CMP-4-1 were shown in FIG. 21.

2) Synthesis of CMP-4-2: Salen-Cu (0.4 mmol), 1,4-diethynylbenzene (1.2 mmol), copper(I) iodide (40 mg) and tetrakis-(triphenylphosphine)palladium(0) (70 mg) were dissolved in a mixture of toluene (12 ml) and triethylamine (4 ml). The reaction mixture was refluxed at 80° C. for 72 hours, yielding the needed compound CMP-4-2.

3) Synthesis of CMP-4-3: Salen-Cu (0.45 mmol), tetrakis (4-ethynylphenyl)methane (1.35 mmol), copper(I) iodide (40 mg) and tetrakis-(triphenylphosphine)palladium(0) (80 mg) were dissolved in a mixture of toluene (15 ml) and triethylamine (5 ml). The reaction mixture was refluxed at 85° C. for 72 hours, yielding the needed compound CMP-4-3.

3. Catalyzing for the Coupling Reaction of $CO_2$ and Epoxides:
1) A mixture of 100 mg CMP-4-1, 400 mg TBAB and 1.75 ml propylene oxide was stirred for 72 hours in $CO_2$ at ambient pressure and temperature, and the yield of the propylene carbonate is 58.5%;

2) A mixture of 100 mg CMP-4-1, 500 mg TBAB and 1.75 ml propylene oxide was stirred for 48 hours in $CO_2$ at ambient pressure and temperature, and the yield of the propylene carbonate is 51.3%;

3) A mixture of 100 mg CMP-4-1, 200 mg TBAB and 1.75 ml propylene oxide was stirred for 48 hours in $CO_2$ at ambient pressure and temperature, and the yield of the propylene carbonate is 42.7%;

4) With 3.0 MPa $CO_2$ introduced, a mixture of 100 mg CMP-4-1, 600 mg TBAB and 1.75 ml propylene oxide was stirred for 2 hours at 100° C., and the yield of the propylene carbonate is 52.7%.

Example 8

Synthesis of CMP-5-1 and its Catalyzation for the Coupling Reaction of $CO_2$ and Epoxides:
1) Synthesis of Salen: with methanol as solvent, a mixture of salicylaldehyde (6.0 mmol) and 1,2-diaminocyclohexane (7.0 mmol) was stirred at 40° C. for 5 hours, yielding the Salen compound;

2) A mixture of salen (3.0 mmol), 1,3,5-triethynylbenzene (1.0 mmol), copper(I) iodide (10 mg) and tetrakis-(triphenylphosphine)palladium(0) (10 mg) was stirred at 30° C. for 60 hours, yielding the target polymer CMP;

3) A mixture of CMP (20 mg) and AlEt$_3$ (20 mg) was stirred and refluxed at 90° C. for 8 hours, yielding the target catalyst compound CMP-5-1.

4) Catalyzing the coupling reaction of $CO_2$ and epoxides:
With sufficient $CO_2$ introduced, a mixture of 10 mg CMP-5-1 and 10 mg propylene oxide (mole ratio of ammonium salt and propylene oxide=1:5) was stirred at 0° C. for 2 hours, the yield of the propylene carbonate is 30%.

Example 9

Synthesis of CMP-5-1 and its Catalyzation for the Coupling Reaction of $CO_2$ and Epoxides:
1) Synthesis of Salen: with methanol as solvent, a mixture of salicylaldehyde (6.0 mmol) and 1,2-diaminocyclohexane (7.0 mmol) was stirred at 40° C. for 5 hours, yielding the Salen compound;

2) A mixture of salen (3.0 mmol), 1,3,5-triethynylbenzene (1.0 mmol), copper(I) iodide (10 mg) and tetrakis-(triphenylphosphine)palladium(0) (10 mg) was stirred at 30° C. for 60 hours, yielding the target polymer CMP;

3) A mixture of CMP (20 mg) and $AlCl_3$ (20 mg) was stirred and refluxed at 90° C. for 8 hours, yielding the target catalyst compound CMP-Al.

4) Catalyzing the coupling reaction of $CO_2$ and epoxides:

With sufficient $CO_2$ introduced, a mixture of 10 mg CMP-5-1 and 10 mg propylene oxide (mole ratio of ammonium salt and propylene oxide=1:5) was stirred at 0° C. for 5 hours, the yield of the propylene carbonate is 39.8%.

Example 10

Synthesis of CMP-5-1 and its Catalyzation for the Coupling Reaction of $CO_2$ and Epoxides:

1) Synthesis of Salen: with propanol as solvent, a mixture of $^t$Bu-substituted salicylaldehyde (6.0 mmol) and 1,2-diaminocyclohexane (7.0 mmol) was stirred at 50° C. for 5 hours, yielding the Salen compound;

2) A mixture of salen (3.0 mmol), 1,3,5-triethynylbenzene (1.0 mmol), copper(I) iodide (10 mg) and tetrakis-(triphenylphosphine)palladium(0) (10 mg) was stirred at 30° C. for 60 hours, yielding the target polymer CMP;

3) A mixture of CMP (20 mg) and $AlBr_3$ (20 mg) was stirred and refluxed at 90° C. for 8 hours, yielding the target catalyst compound CMP-Al.

4) Catalyzing the coupling reaction of $CO_2$ and epoxides:

With sufficient $CO_2$ introduced, a mixture of 10 mg CMP-5-1 and 10 mg propylene oxide (mole ratio of ammonium salt and propylene oxide=1:5) was stirred at 0° C. for 10 hours, the yield of the propylene carbonate is 52.1%.

Example 11

Synthesis of CMP-5-1 and its Catalyzation for the Coupling Reaction of $CO_2$ and Epoxides:

1) Synthesis of Salen: with methanol as solvent, a mixture of Cl-substituted salicylaldehyde (6.0 mmol) and 1,2-diaminocyclohexane (7.0 mmol) was stirred at 25° C. for 5 hours, yielding the Salen compound;

2) A mixture of salen (3.0 mmol), 1,3,5-triethynylbenzene (1.0 mmol), copper(I) iodide (10 mg) and tetrakis-(triphenylphosphine)palladium(0) (10 mg) was stirred at 30° C. for 60 hours, yielding the target polymer CMP;

3) A mixture of CMP (20 mg) and $AlEt_3$ (20 mg) was stirred and refluxed at 140° C. for 8 hours, yielding the target catalyst CMP-5-1;

4) Catalyzing the coupling reaction of $CO_2$ and epoxides:

With sufficient $CO_2$ introduced, a mixture of 10 mg CMP-5-1 and 10 mg propylene oxide (mole ratio of ammonium salt and propylene oxide=1:5) was stirred at 0° C. for 20 hours, the yield of the propylene carbonate is 63.4%.

Example 12

Synthesis of CMP-5-1 and its Catalyzation for the Coupling Reaction of $CO_2$ and Epoxides:

1) Synthesis of Salen: with methanol as solvent, a mixture of Cl-substituted salicylaldehyde (6.0 mmol) and 1,2-diaminocyclohexane (7.0 mmol) was stirred at 25° C. for 5 hours, yielding the Salen compound;

2) A mixture of salen (3.0 mmol), 1,3,5-triethynylbenzene (1.0 mmol), copper(I) iodide (10 mg) and tetrakis-(triphenylphosphine)palladium(0) (10 mg) was stirred at 30° C. for 60 hours, yielding the target polymer CMP;

3) A mixture of CMP (20 mg) and $AlCl_3$ (20 mg) was stirred and refluxed at 90° C. for 8 hours, yielding the target catalyst compound CMP-5-1;

4) Catalyzing the coupling reaction of $CO_2$ and epoxides:

With sufficient $CO_2$ introduced, a mixture of 10 mg CMP-5-1 and 10 mg propylene oxide (mole ratio of ammonium salt and propylene oxide=1:5) was stirred at 10° C. for 6 hours, the yield of the propylene carbonate is 40.3%.

Example 13

Synthesis of CMP-5-1 and its Catalyzation for the Coupling Reaction of $CO_2$ and Epoxides:

1) Synthesis of Salen: with methanol as solvent, a mixture of $NO_2$-substituted salicylaldehyde (6.0 mmol) and 1,2-diaminocyclohexane (7.0 mmol) was stirred at 50° C. for 10 hours, yielding the Salen compound;

2) A mixture of salen (3.0 mmol), 1,3,5-triethynylbenzene (1.0 mmol), copper(I) iodide (10 mg) and tetrakis-(triphenylphosphine)palladium(0) (10 mg) was stirred at 30° C. for 60 hours, yielding the target polymer CMP;

3) A mixture of CMP (100 mg) and $AlEt_3$ (20 mg) was stirred and refluxed at 90° C. for 8 hours, yielding the target catalyst CMP-5-1;

4) Catalyzing the coupling reaction of $CO_2$ and epoxides:

With sufficient $CO_2$ introduced, a mixture of 10 mg CMP-5-1 and 10 mg propylene oxide (mole ratio of ammonium salt and propylene oxide=1:5) was stirred at 0° C. for 5 hours, the yield of the propylene carbonate is 53.5%.

Example 14

Synthesis of CMP-5-1 and its Catalyzation for the Coupling Reaction of $CO_2$ and Epoxides:

1) Synthesis of Salen: with i-propanol as solvent, a mixture of $^i$Bu-substituted salicylaldehyde (6.0 mmol) and 1,2-diaminocyclohexane (7.0 mmol) was stirred at 70° C. for 5 hours, yielding the Salen compound;

2) A mixture of salen (3.0 mmol), 1,3,5-triethynylbenzene (1.0 mmol), copper(I) iodide (10 mg) and tetrakis-(triphenylphosphine)palladium(0) (10 mg) was stirred at 30° C. for 60 hours, yielding the target polymer CMP;

3) A mixture of CMP (100 mg) and $AlBr_3$ (20 mg) was stirred and refluxed at 90° C. for 8 hours, yielding the target catalyst compound CMP-5-1.

4) Catalyzing the coupling reaction of $CO_2$ and epoxides:

With sufficient $CO_2$ introduced, a mixture of 10 mg CMP-5-1 and 10 mg propylene oxide (mole ratio of ammonium salt and propylene oxide=1:5) was stirred at 15° C. for 20 hours, the yield of the propylene carbonate is 83.7%.

Example 15

Synthesis of CMP-5-1 and its Catalyzation for the Coupling Reaction of $CO_2$ and Epoxides:

1) Synthesis of Salen: with i-propanol as solvent, a mixture of $^i$Bu-substituted salicylaldehyde (6.0 mmol) and 1,2-diaminocyclohexane (7.0 mmol) was stirred at 70° C. for 5 hours, yielding the Salen compound;

2) A mixture of salen (3.0 mmol), 1,3,5-triethynylbenzene (1.0 mmol), copper(I) iodide (10 mg) and tetrakis-(triphenylphosphine)palladium(0) (10 mg) was stirred at 30° C. for 60 hours, yielding the target polymer CMP;

3) A mixture of CMP (20 mg) and $Al(OEt)_3$ (20 mg) was stirred and refluxed at 90° C. for 8 hours, yielding the target catalyst CMP-5-1.

4) Catalyzation for the coupling reaction of $CO_2$ and epoxides:

With sufficient $CO_2$ introduced, a mixture of 10 mg CMP-5-1 and 30 mg propylene oxide (mole ratio of ammonium salt and propylene oxide=1:10) was stirred at 0° C. for 5 hours, the yield of the propylene carbonate is 68.2%.

Example 16

Synthesis of CMP-5-1 and its Catalyzation for the Coupling Reaction of $CO_2$ and epoxides:

1) Synthesis of Salen: with hexanol as solvent, a mixture of $CH_2N(CH_3)_2CH_2Ph$-substituted salicylaldehyde (6.0 mmol) and 1,2-diaminocyclohexane (7.0 mmol) was stirred at 80° C. for 5 hours, yielding the Salen compound;

2) A mixture of salen (3.0 mmol), 1,3,5-triethynylbenzene (1.0 mmol), copper(I) iodide (10 mg) and tetrakis-(triphenylphosphine)palladium(0) (10 mg) was stirred at 30° C. for 60 hours, yielding the target polymer CMP;

3) A mixture of CMP (20 mg) and $Al(OMe)_3$ (20 mg) was stirred and refluxed at 90° C. for 8 hours, yielding the target catalyst compound CMP-Al.

4) Catalyzing the coupling reaction of $CO_2$ and epoxides:

With sufficient $CO_2$ introduced, a mixture of 10 mg CMP-5-1 and 30 mg propylene oxide (mole ratio of ammonium salt and propylene oxide=1:5) was stirred at 0° C. for 13 hours, the yield of the propylene carbonate is 89.6%.

Example 17

Synthesis of CMP-5-1 and its catalyzation for the coupling reaction of $CO_2$ and epoxides:

1) Synthesis of Salen: with butanol as solvent, a mixture of $CH_2N(Bn)Et_2Br$-substituted salicylaldehyde (6.0 mmol) and 1,2-diaminocyclohexane (7.0 mmol) was stirred at 25° C. for hours, yielding the Salen compound;

2) A mixture of salen (3.0 mmol), 1,3,5-triethynylbenzene (1.0 mmol), copper(I) iodide (10 mg) and tetrakis-(triphenylphosphine)palladium(0) (10 mg) was stirred at 30° C. for 60 hours, yielding the target polymer CMP;

3) A mixture of CMP (20 mg) and $Al(OMe)_3$ (20 mg) was stirred and refluxed at 100° C. for hours, yielding the target catalyst CMP-5-1.

4) Catalyzing the coupling reaction of $CO_2$ and epoxides:

With sufficient $CO_2$ introduced, a mixture of 10 mg CMP-5-1 and 30 mg propylene oxide (mole ratio of ammonium salt and propylene oxide=1:5), was stirred at 0° C. for 20 hours, the yield of the propylene carbonate is 93.5%.

Using the polymers as catalysts to catalyze the coupling reaction of CO2 and epoxides, the yields of the cyclic carbonates were in the range of 35~90%. The catalysts can be reused for several times without reducing the yields which can reach to 90% above at high pressure (2~8 MPa) and the temperature of 50~120° C. for 1~3 hours. The procedure is a breakthrough for overcoming the limitation of this reaction which can only occur at high pressure and temperature catalyzed by other catalysts. Meanwhile the reuse of the catalysts can figure out the troubles caused by the low efficiency of the other catalysts.

The invention claimed is:

1. A cobalt conjugated microporous polymer catalyst having the following structure designated as CMP1-1:

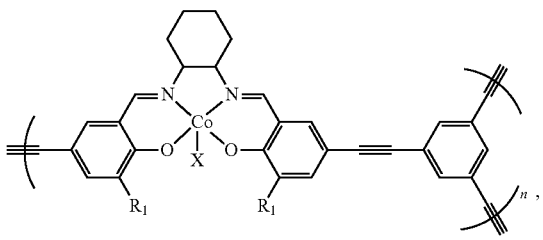

wherein, $R_1$=—H, —$^tBu$, —$^iBu$, —$NO_2$, —Cl, —$CH_2NEt_2$, —$CH_2N(Bn)Et_2Br$, —$CH_2N(CH_3)_2CH_2Ph$,

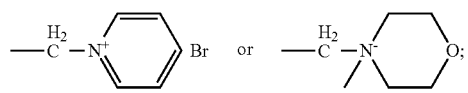

X=—OAc or —Cl or —Br or —I or -Et or —OMe or —OEt or —$OCH_2CH_2(OCH_2CH)_2Cl$, and the degree of polymerization for the synthesized conjugated catalyst CMP1-1 is in the range of 30~100.

2. A method for preparing the conjugated polymer catalyst CMP-1-1 of claim 1 comprising:
synthesis of the conjugated microporous polymer catalyst CMP-1-1: with anhydrous toluene and TEA as solvent (volume ratio=3~4:1), CuI and tetrakis-(triphenylphosphine)palladium(0) as catalyst, a mixture solution of 1,3,5-triethynylbenzene and Salen-Co-X, (mole ratio=1~4:1) is stirred under argon for 60~90 hours at 25~100° C., affording the CMP-1-1, wherein the mole ratio of CuI and alkynyl benzene A is 1:5~10 and, the mole ratio of tetrakis-(triphenylphosphine)palladium(0) and alkynyl benzene A is 1:20~30.

3. The method of claim 2 wherein:
the amount of anhydrous toluene required by each 1 mmol Salen-Co X, S is 30~50 ml.

4. A method of making a cyclic carbonate comprising coupling $CO_2$ and an epoxide in the presence of the catalyst of claim 1 at 0~180° C. and 0.1~8.0 MPa $CO_2$ pressure.

5. The method of claim 4,
for the catalytic reaction of $CO_2$ and epoxides at ambient pressure and temperature comprising in the presence of an amine compound, a mixture solution of CMP-1-1 and an epoxide (mass ratio=1:10~50) is stirred for 12~72 hours at ambient pressure and temperature, affording the corresponding cyclic carbonates, wherein the mole ratio of the amine compound and epoxide is 1:10~100.

6. The method of claim 5, wherein, the amine compound is selected from quaternary ammonium salt of tetrabutyl ammonium chloride, tetrabutyl ammonium bromide, tetrabutyl ammonium iodide and tetrabutyl ammonium acetate, a tertiary triethylamine (TEA), and dimethylaminopyridine (DMAP).

7. The method of claim 5, wherein, the epoxide is selected from the group consisting of propylene oxide, epichlorohydrin, 2-ethyloxirane, 2-butyloxirane, and 2-phenyloxirane.

8. The method of claim 4 for the catalytic reaction of $CO_2$ and epoxides at a high temperature and a high pressure comprising in the presence of an amine compound, a mixture solution of CMP-1-1 and an epoxide (mass ratio=1:10~50) is stirred for 1~6 hours at 50~160° C. and 2~8 MPa $CO_2$ pressure, affording the corresponding cyclic carbonates, wherein, the mole ratio of amine compounds and epoxides is 1:10~100.

* * * * *